US010996214B2

(12) United States Patent
Shaked et al.

(10) Patent No.: US 10,996,214 B2
(45) Date of Patent: May 4, 2021

(54) INTERFEROMETRIC SYSTEM AND METHOD FOR USE WITH BIOLOGICAL CELLS AND ORGANISMS INCLUDING SPERM

(71) Applicant: Technology Innovation Momentum Fund (Israel) Limited Partnership, Tel Aviv (IL)

(72) Inventors: Natan Tzvi Shaked, Mazkeret Batya (IL); Pinhas Girshovitz, Beer Sheva (IL); Itay Barnea, Petach Tikva (IL); Michal Balberg, Jerusalem (IL); Simcha Mirsky, Petach Tikva (IL); Pinkie Jacob Eravuchira, Tel Aviv (IL)

(73) Assignee: TECHNOLOGY INNOVATION MOMENTUM FUND (ISRAEL) LIMITED PARTNERSHIP, Tel Aviv (IL)

( * ) Notice: Subject to any disclaimer, the term of this patent is extended or adjusted under 35 U.S.C. 154(b) by 732 days.

(21) Appl. No.: 15/420,445

(22) Filed: Jan. 31, 2017

(65) Prior Publication Data

US 2017/0205390 A1 Jul. 20, 2017

Related U.S. Application Data

(63) Continuation-in-part of application No. PCT/IL2016/050478, filed on May 5, 2016.

(60) Provisional application No. 62/158,073, filed on May 7, 2015.

(51) Int. Cl.
| | | |
|---|---|---|
| *G01N 33/487* | (2006.01) | |
| *G01N 15/14* | (2006.01) | |
| *G01N 21/45* | (2006.01) | |
| *B01L 3/00* | (2006.01) | |
| *G01B 9/02* | (2006.01) | |
| *G01B 11/24* | (2006.01) | |
| *G01N 15/10* | (2006.01) | |
| *G01N 21/23* | (2006.01) | |

(52) U.S. Cl.
CPC .... *G01N 33/48728* (2013.01); *B01L 3/50273* (2013.01); *B01L 3/502715* (2013.01); *B01L 3/502761* (2013.01); *G01B 9/02041* (2013.01); *G01B 11/2441* (2013.01); *G01N 15/1434* (2013.01); *G01N 15/1468* (2013.01); *G01N 15/1475* (2013.01); *G01N 21/453* (2013.01); *B01L 2200/0647* (2013.01); *B01L 2200/10* (2013.01); *B01L 2300/0864* (2013.01); *B01L 2300/0877* (2013.01); *B01L 2300/14* (2013.01); *G01N 21/23* (2013.01); *G01N 2015/1006* (2013.01); *G01N 2015/1454* (2013.01)

(58) Field of Classification Search
None
See application file for complete search history.

(56) References Cited

U.S. PATENT DOCUMENTS

| 8,842,901 | B2 | 9/2014 | Ozcan et al. |
| 2004/0089798 | A1 | 5/2004 | Gruber et al. |
| 2009/0125242 | A1 | 5/2009 | Choi et al. |
| 2015/0049343 | A1 | 2/2015 | Shaked et al. |

FOREIGN PATENT DOCUMENTS

| CN | 1774623 A | 5/2006 |
| JP | 2005521425 | 7/2005 |
| WO | 03/085379 | 10/2003 |
| WO | 2013/140396 | 9/2013 |

OTHER PUBLICATIONS

Coppola, Gianluca, et al. "Digital holographic microscopy for the evaluation of human sperm structure." arXiv preprint arXiv: 1307.3445 (2013).*
Patrascu, et al., Optimized morphologic evaluation of biostructures by examination in polarized light and differential interference contrast microscopy, Romanian Journal of Legal Medicine, Dec. 1, 2014, pp. 275-282, vol. 22, No. 4.
Boland, et al., Automated Recognition of Patterns Characteristic of Subcellular Structures in Fluorescence Microscopy Images, Cytometry, 1998, pp. 366-375, vol. 33.
Crha, et al., Digital holographic microscopy in human sperm imaging, J. Assist. Reprod. Genet., 2011, pp. 725-729, vol. 28.
Di Caprio, et al., 4D tracking of clinical seminal samples for quantitative characterization of motility parameters, Biomedical Optics Express, 2014, pp. 690-700, vol. 5, No. 3.
Deng, Lijun, Digital holographic microscopy and study on the several application technologies, Basic science series of China Doctor's Theses, Apr. 15, 2015.
Di Caprio, et al., Quantitive Label-Free Animal Sperm Imaging by Means of Digital Holographic Microscopy, Journal of Selected Topics in Quantum Electronics, Jul./Aug. 2010, pp. 833-840, vol. 16, No. 4.

* cited by examiner

*Primary Examiner* — G Steven Vanni
(74) *Attorney, Agent, or Firm* — Browdy and Neimark, P.L.L.C.

(57) ABSTRACT

Methods and systems for use in sperm analysis are described. A method for processing measured data comprising at least interferometric phase data of label-free sperm cell(s), the processing comprising determining topographic optical phase delay map of the label-free sperm, determining at least one physical parameter of the label-free sperm, and generating data indicative of sperm quality for the label-free sperm. A device comprising a flow channel comprising an inlet for receiving fluid containing cells, a selection zone and at least two outlets at said selection zone; and a flow-driving mechanism comprising a flow-driving unit configured and operable to generate flow of said fluid from said inlet towards at least first of said at least two outlets, and a collecting driving unit selectively operating along the direction of a second outlet of said at least two outlets to direct a portion of interest of said fluid towards said second outlet.

20 Claims, 10 Drawing Sheets

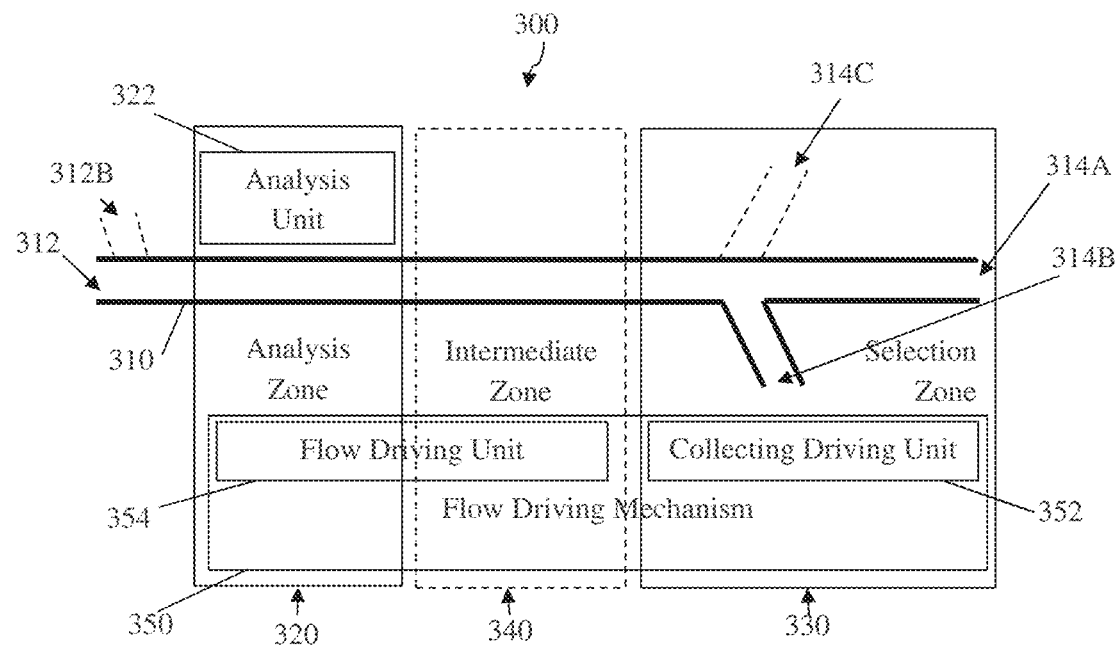
Fig. 3A
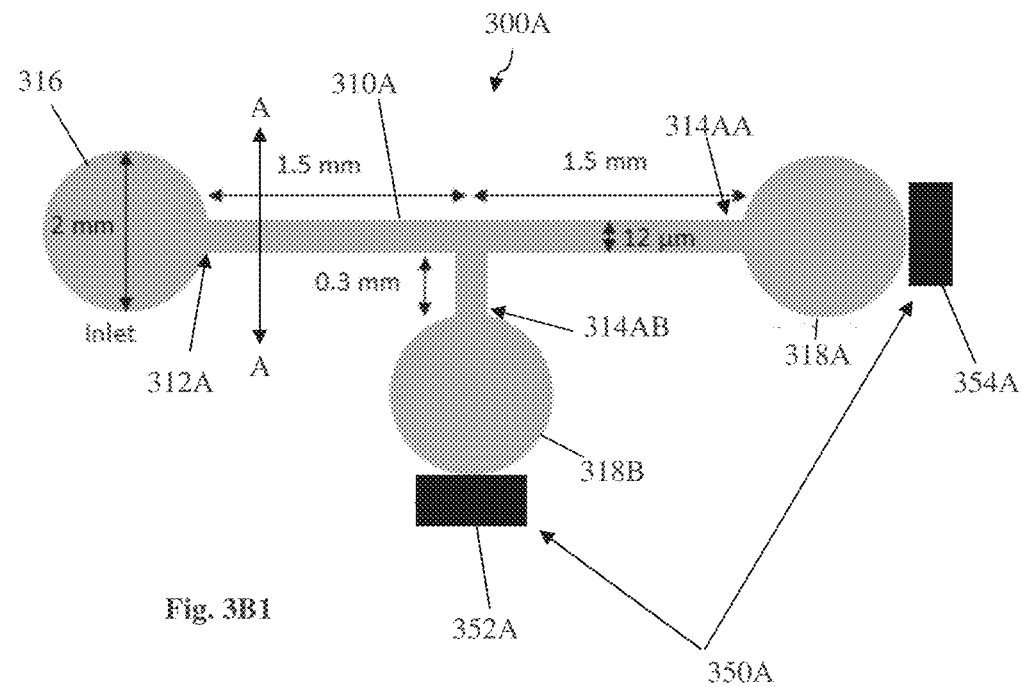
Fig. 3B1

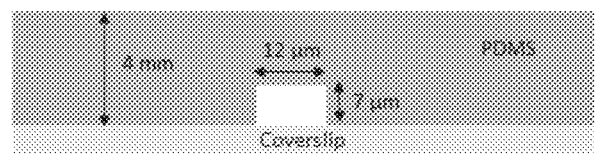
Fig. 3B2
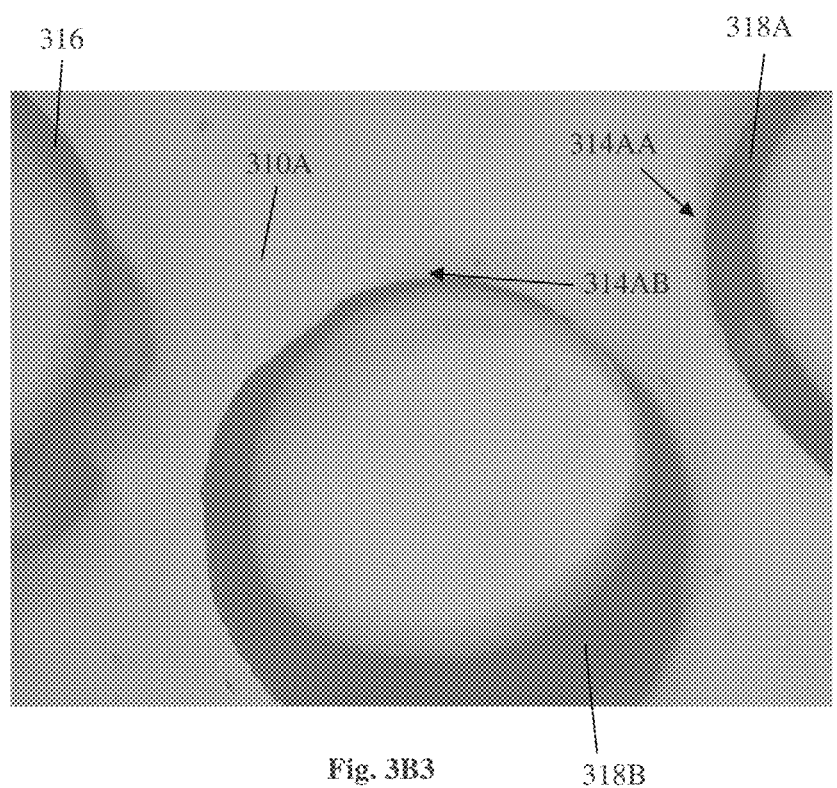
Fig. 3B3

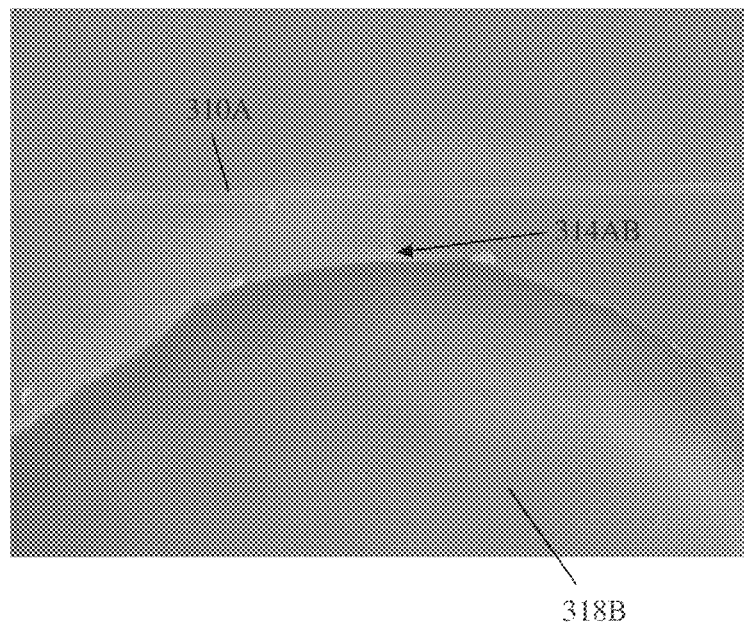
Fig. 3B4
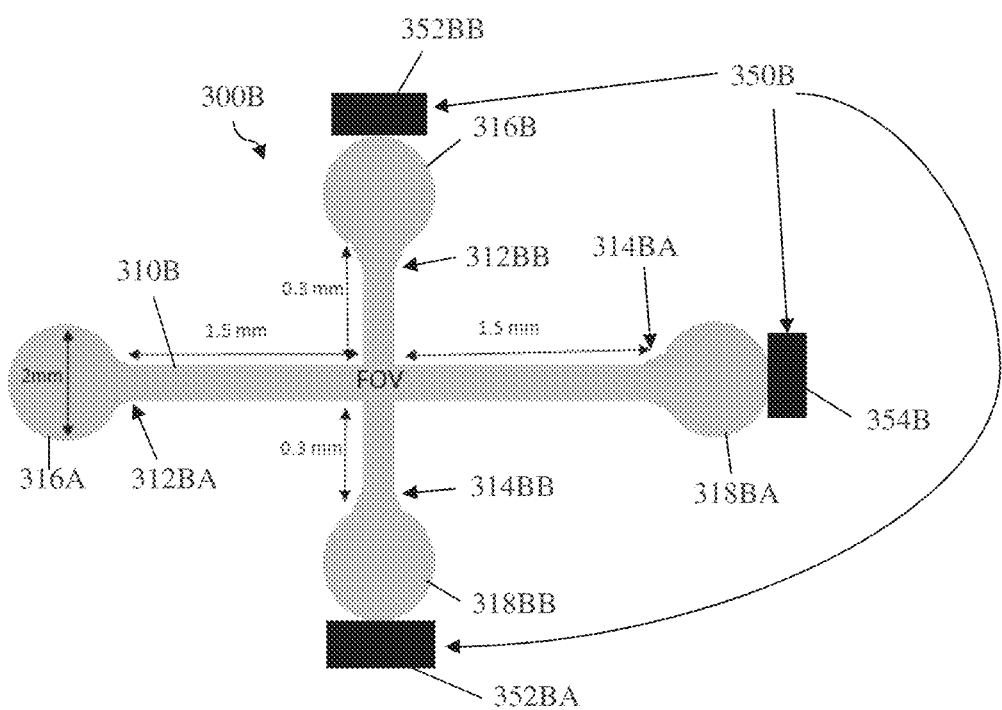
Fig. 3C1

Fig. 3C2

INTERFEROMETRIC SYSTEM AND METHOD FOR USE WITH BIOLOGICAL CELLS AND ORGANISMS INCLUDING SPERM

RELATED APPLICATIONS

This is a Continuation-in-Part of Application No. PCT/IL2016/050478 filed May 5, 2016, which claims the benefit of U.S. Provisional Application No. 62/158,073 filed May 7, 2015. The disclosures of each of these prior art applications are hereby incorporated by reference herein in their entirety.

TECHNOLOGICAL FIELD

The invention relates generally to interferometric systems and methods of optical analysis of biological cells and organisms. Specifically, the invention is useful for interferometric analysis and selection of individual sperm samples to be used in in-vitro fertilization procedures.

BACKGROUND

Approximately 70 million people worldwide need assisted reproductive techniques (ART) to bare children. Following the introduction of in-vitro fertilization (IVF), several efforts have been directed towards identifying the oocyte's and fetus's morphologies as a prognostic tool for IVF success. Works were also conducted on the ability of sperm cell morphology to predict the success rates of natural fertilization, intra-uterine insemination, IVF and IVF with intra-cytoplasmatic sperm injection (ICSI), in which a single sperm cell is selected, based on its mobility and overall morphology, using high magnification phase contrast microscope and the selected sperm cell is injected directly into the oocyte retrieved from the female partner. It has been found that sperm morphology is a good predictor for fertilization success and patients with abnormal semen analysis had lower probability of successful pregnancies using IVF. ICSI is the only treatment solution, known to date, for severe male factor infertility. In spite of this, the success rate of ICSI (measured by clinical pregnancy or live birth rate) is still very low, only about 20% of patients undergoing IVF with ICSI succeed in achieving pregnancy. Moreover, several clinical studies have shown that the percentage of chromosomal abnormalities in fetuses and babies conceived using ICSI is higher than in the general population, and even compared to other ART procedures. Ideally, the sperm that is chosen for ICSI should have the highest chance of successful fertilization and subsequent embryo growth. The viability of the sperm cell to be used in ICSI procedure is maintained by diagnostic modalities which are label-free and which do not involve any kind of stain.

One of the known and common techniques for evaluating sperm cell morphological parameters is the qualitative, non-quantitative, label-free bright field microscopy (BFM). Typically, sperm cells are imaged optically using BFM and chosen according to the world health organization (WHO) guidelines. Therefore, a morphological examination of about 200 fixated, stained cells is conducted for the evaluation of properties such as the size of the nucleus and the acrosome. The images are then analyzed visually by an experienced embryologist, or using a software (computer assisted sperm analysis (CASA)) that automatically measures the different morphological features. Without staining, sperm cells are nearly transparent under BFM, since their optical properties are only slightly different from their surroundings, resulting in a weak image contrast. Recently, new methods were developed for identifying finer properties of the sperm cell, not seen by BFM (e.g. surface charge selection). Most of these methods involve biochemical preparations that might change the viability of the cells and thus precluding their use in IVF.

Phase imaging methods use the optical interference phenomenon to record the light delays when passing through the sample, and are able to create label-free contrast in the image. Conventional phase-contrast imaging methods for sperm cells were developed, such as Zernike's phase contrast and Nomarski's differential interference contrast (DIC). DIC is the basis for the motile sperm organelle morphology examination (MSOME) technique. DIC enhances the image edges by shadowing, and thus enables to see details not seen on normal label-free BFM. However, both Zernike's phase contrast and DIC techniques are not fully quantitative, since they do not create meaningful contrast on all points of the measured sperm. In addition, these techniques present significant imaging artifacts, especially near the cell edges, which might yield wrong morphological assays.

Current techniques for examining a sperm cell to identify whether it is suitable for the above procedures, such as ICSI, include visualizing the sperm cells with a X10-X40 phase microscope. In this magnification, the sperm morphology cannot be visualized well, and accordingly the sperm selection, which is done by catching a single sperm cell using a very small-tip pipette connected into mechanical controller (e.g. micro-manipulator), is challenging.

GENERAL DESCRIPTION

There is a need in the art for a novel technique for analysis (e.g., imaging) and/or selection of a biological sample. In one aspect, the present invention provides novel techniques for imaging/analyzing/examining biological samples and classifying them by quantitatively determining morphological parameters of a biological sample. Specifically, the invention provides a novel technique which is useful in obtaining quantitative and three-dimensional physical analysis, of unstained (so called unlabeled, or label-free) biological samples or cells, with very high accuracy. In another aspect, the present invention provides a novel technique in sorting biological samples, which have been analyzed and classified, such that the chosen ones are collected, enabling using them for the intended purpose. The sorting of biological samples/cells is done on the spot, one by one, immediately after the examination (e.g., by optical imaging), and decision making about whether a specific biological sample/cell is chosen or not.

The invention enables, for example, quantifying morphological parameters of live unlabeled sperm cells and quantitatively scoring of the sperm cells. The technique of the invention would enable better selection of sperm cells for intra-cytoplasmatic sperm injection (ICSI) procedures, resulting in higher pregnancy rates and potentially avoiding genetic disorders in the resulting offspring. Although the invention is exemplified herein with regard to sperm cells, it should be understood that the principles of the invention are not limited to any specific type of biological samples/cells and may be used for any type of such samples/cells such as cancer cells.

During selection of the best sperm cell for using in ICSI, several physical or morphological parameters, preferably in quantitative measures, are explored, such as the size, length and width of the sperm head, neck, midpiece and acrosome, tail configuration and a general normality of the cell sperm cell head.

When applying optical imaging/measurements to biological samples, e.g. sperm cells, a light beam that passes through the sperm cells is delayed as compared to that of the surroundings, since the cells have a slightly higher refractive index than their surroundings. Accordingly, the refractive index of the biological sample presents an internal optical contrast mechanism which may be exploited during examination procedures of the biological sample/sperm cell. However, regular intensity-based detectors are not fast enough to record this delay directly.

Interferometric phase microscopy (IPM) is capable of providing fully quantitative, phase-contrast image data. IPM is a holographic imaging method, which allows for quantitative measurement of the sample/cell optical thickness (OPD, i.e. the product of refractive index and physical thickness). It should be understood that the terms optical thickness and OPD, used herein, are the same and are used through the text interchangeably. Recently, several initial researches have demonstrated utilization of IPM (also called digital holographic microscopy) for sperm characterization. In one research, IPM was used to evaluate sperm, mainly based on the presence or absence of vacuoles. Since the vacuoles form early in spermatogenesis, they may reflect defects in sperm content, and therefore these cells should be avoided in ICSI. Using IPM, it was shown that vacuolated cells have a decreased volume. Another research compared normal and pathological sperm samples with IPM, and it was shown that abnormal sperm heads have lower maximal optical path difference (i.e. the OPD) compared to normal samples. The present invention provides a method and system for assessing the quality of the sperm cell (e.g. for fertility potential examination) by creating an objective and quantitative quality score based on IPM measurements of a label-free cell, and possibly on additional measurements. The quantitative quality score can be used to identify sperm cells suitable for use in IVF. According to the present invention, IPM-based methods are used to quantify sperm morphology and to identify the cellular compartments which play significant role in the fertility potential (e.g. the acrosome and the nucleus) based on the OPD data, and on the spatial distribution of the dry mass of the sperm cell (the mass of the sperm cell's tissues/dry composition without water/fluid) between the cellular compartments which is obtained directly from the OPD data.

Thus, IPM can be used to quantify sperm morphology without staining and to differentiate between the acrosomal and the nuclear compartments, and other morphological and physiological structures (e.g. vacuoles) in a live, unlabeled sperm cell. The present invention also provides equivalent information to bright field microscopy (BFM) imaging of stained sperm cells when measuring key morphologic parameters of fixed human spermatozoa according to the World Health Organization (WHO) criteria, thus paving the way for directly selecting label-free sperm cells for IVF and ICSI.

According to the present invention, one of the main parameters that are used to score the sperm cell is a topographic OPD map corresponding to each point on the imaged biological sample/cell, such that the value of each pixel in a digital IPM image corresponds to the OPD for that pixel. Other parameters for scoring the sperm cell may be a topographic dry mass map, topographic height map, topographic refractive index map and topographic birefringence map. The score of the sperm cell may utilize all or some of the aforementioned maps, to assess, by quantification, the quality score of the label-free sperm cell, e.g. for fertility examination procedure.

The topographic height map, i.e. the physical thickness map, may be obtained from the OPD map by knowing the refractive indices of the corresponding different organs/regions of the sperm cell. Alternatively, an atomic force microscope can be used to measure the physical thickness of dehydrated, fixated, un-labeled sperm cells and obtain the average refractive indices of each location within a sperm cell.

The measurements and/or calculation of the dry mass and/or refractive indices allow the construction of a database of dry mass of the several organelles/compartments in the sperm cell, and a data base of refractive indices of normal and abnormal cells and their cellular compartments, enabling to quantify sperm potency for fertilization. It should be noted that for a given physical thickness, the OPD of the cell, and its compartments, is linearly dependent on the refractive index of the cell relative to the surrounding medium. As cells are mainly composed of water, it is possible to calculate the dry mass of the cell (i.e. the average mass of the proteins, carbohydrates, lipids etc. within the cell) using the OPD when the cells are immersed in liquid with a refractive index similar to that of water. Specifically, the human spermatozoa head comprises two general compartments, which differ significantly in the composition and concentration of proteins, nucleic acids and other components: the nucleus and the acrosome. The acrosomal part contains an array of hydrolytic enzymes necessary for digesting the zona pellucida during penetration of the oocyte, whereas the nucleus comprises the DNA, the related proteins, enzymes and lipids. Consequently, the dry mass of these cellular compartments will differ due to their different composition.

The topographic birefringence map may also be included in the quality score of the sperm cell to assess DNA quality. DNA fragmentation may be associated with a poor outcome for fertilization, implantation and fetal development. A recent study demonstrated that patients with a predominance of abnormal acrosomes had a significantly greater percentage of sperm with DNA fragmentation compared with the controls. Optical measurement, using a polarization microscope, demonstrated that the birefringence distribution (total or partial) of sperm heads is correlated with DNA fragmentation. In particular, cells with a total birefringence coverage of the sperm head show DNA fragmentation. As birefringence is related to the spatial order of the proteins and nucleic acids within the organelles, their findings relate to variations in the birefringence of the acrosomal and nuclear parts of the cells, and cells without an acrosome will show a total birefringence.

IPM is advantageous because it requires low power resources and presents high throughput since capturing is done in a single exposure and without scanning. However, IPM setups are usually bulky, expensive, and hard to operate. A simple, portable, compact and inexpensive IPM has been developed by some inventors of the present invention and is described in WO 2013/140396. This interferometric device provides a substantially stable, easy to align common path interferometric geometry, while eliminating a need for controllably changing the optical path of the beam. The interferometric device can be used for acquiring images of live biological cells in a label-free manner with sub-nanometric thickness precision. The device can be easily used with any microscope.

In contrast to other non-quantitative techniques, IPM can yield the cell optical thickness (i.e., physical thickness× refractive index) profile for each point on the measured cell. The present invention provides a fast and effective quantitative analysis of biological organisms, such as sperm cells, without a need for labeling the sample being analyzed, based on a novel data interpretation technique. It should be noted that, generally, the interpretation of the IPM results is difficult due to the decoupling between the refractive index and the physical thickness of the cell.

In addition, the present invention provides other information that can be of interest to the fertilizing potential of the sperm cell. Since IPM measures the optical thickness of the cell, which is the product of the refractive index and the physical thickness, one can extract any of these parameters by assuming the other one. Also, according to the present invention, the dry mass parameter, which can be calculated based on the OPD, is utilized in addition to the OPD, to generate the quality score of the sperm cell that is related to measurable physical properties of the cell and its compartments.

As said, according to the present invention, the quantitative scoring analysis of in the sperm cell may use unique morphological quantitative parameters, which are based on the three-dimensional morphology of the sperm cell, as obtained from the OPD measurements. To derive the parameters, IPM measurements may be done firstly on one or more sperm cells which are labeled in order to define the cell organelles transverse locations and a training database is built to obtain a characteristic OPD map which includes, inter alia, the characteristic refractive indices of the various organelles inside a sperm cell. According to the invention, the characteristic refractive indices of different organelles, e.g. the vacuoles, are determined, inter alia, by an IPM measurement performed on the labeled sperm cells immersed in mediums of known refractive indices. A two-dimensional OPD map defined by the product of the sperm physical thickness and the refractive index map (distribution) allows determining the refractive index and physical thickness (height) in each point (in the image plane) of the sperm and specifically at the different locations of the organelles. The refractive indices of the various organelles in a sperm cell are considered to have relatively constant values. Accordingly, a two-dimensional map of refractive indices for each point in a sperm cell is saved in a database and can be used to obtain a map of the physical thickness (the topographic height map), i.e. a three-dimensional representation, of the whole sperm cell including internal organelles of interest.

Real measurement of the phase map, performed on an unlabeled sperm cell, gives, by using the novel refractive indices map of every point in the sperm cell (i.e. the characteristic refractive index map) stored in database, the physical sperm thickness of the sperm cell, specifically at the different locations of the various organelles.

As explained earlier, since the different quantitative measures (OPD, height, dray mass and birefringence maps) can be obtained independently or from each other, the database can include, in addition to the characteristic refractive index map, either or all of the maps: the OPD map, the dry mass map or the birefringence maps, such that each can be used to calculate the quality score of the sperm cell.

In some embodiments, based on the sperm transverse locations, a computerized thickness map for the sperm head, the sperm neck or any other organelle of interest, is built. Fitting may be used to correlate the expected computerized thickness map with the measured thickness map.

Immersion of the sperm cell in a medium with a specific refractive index may also enhance the contrast when imaging. It is known that the refractive index of the vacuoles is significantly lower than the refractive index of the other cellular contents. If the refractive index of the immersion medium becomes higher than the refractive index of the vacuole (plus the cellular material located above and below it), the contrast in the vacuole location will be inverted. If the sperm cell is put in a medium with a slightly higher refractive index, then an enhanced contrast may be achieved.

As mentioned above, after the analysis stage, the suitable cells can be selected by separating between the chosen and unchosen cells. It is noted that the word "chosen", as used herein, means such a cell which has certain parameters, and so generally speaking, the chosen cell can be the suitable cell for a specific application. However, alternatively, the chosen cell can be the unsuitable cell for the specific application, and thus can be excluded. The imaging/analysis and selection stages are done on each cell individually in a cell-by-cell fashion, resulting in high accuracy collection of the most suitable cells. Generally, a system of the invention comprises at least two distinguished sequential zones, the analysis (e.g. imaging) zone, in which the cells are examined (e.g., optically imaged) and classified, and a decision of yes/no is made during examination and classification stages, and the selection zone, where the cells are sorted during the selection phase, such that the chosen ones are collected in one region, while the unwanted ones are collected in a second region or are not collected. As such, the system of the invention is constructed to enable flow of individual cells in sequence, such that each cell enters the analysis zone to be examined and classified (chosen/not chosen), then it flows and enters the selection zone to be collected into a zone of chosen cells or into a zone of unchosen cells, as the case may be. Generally, the collection in the selection zone is made on either the chosen or unchosen cells. Specifically, the collection in the selection zone is made on the chosen cells.

To this end, the invention provides a system comprising a cell analysis (e.g., imaging) utility and a cell sorting utility. As a non-limiting example, the cell imaging/analysis utility can be an IPM system, utilizing the technique described above. However, it should be noted that any other imaging/analysis system and method can be utilized. The system may comprise one or more channels configured to allow a single cell to be analyzed and then sorted, at a time. One of the suitable channels is a microfluidic channel, which can be specifically manufactured with custom dimensions such that only one cell/biological sample, of the kind undergoing examination and sorting, can pass through its cross section at a given time. The analysis and selection zones are generally located one after the other along the channel(s). The cell flows, either independently or by help of an external force, inside the channel(s), is examined and then sorted. The channel can be connected, at one side, to one or more inlet ports and, at the other side, to two or more outlet ports. The cells enter from one inlet port in sequence and undergo imaging, examination and classification. After exiting the analysis zone, the cell is classified as being a suitable one (chosen) or not suitable (unchosen) to thereby affect its movement, when it enters the selection zone, towards a first outlet, as a chosen cell, or a second outlet as an unchosen cell. The diversion of the movement direction can be applied to both classified cells, chosen and unchosen, or only to one of them. Diverting one or both chosen and unchosen cells may depend on their relative numbers. For example, if the number of chosen cells is much less than the number of unchosen cells, then the diverting mechanism may act only on the chosen cells, while the others keep flowing uninterrupted towards their natural/dedicated outlet. In such case, the movement inside the channel can be from the inlet port to a first outlet port and can be controlled, as needed, by a first constant flow-driving unit. If after analysis (e.g., using optical imaging), while flowing inside the channel, the cell is identified as suitable one, then its status is recorded as "chosen", and its movement is deflected towards a second outlet port by a second flow-driving unit activated temporarily with a larger driving force than the force constantly applied (maintained) by the first constant flow-driving unit.

Thus according to a first broad aspect of the present invention, there is provided a method for use in sperm analysis, the method comprising processing measured data comprising at least interferometric phase data of a label-free sperm cell, said processing of the measured data comprising determining topographic OPD map, determining at least one physical parameter of the label-free sperm cell and generating data indicative of sperm quality for the label-free sperm cell.

In some embodiments, the processing of the measured data further comprises generating a topographic dry mass map of the label-free sperm cell.

In some embodiments, the processing of the measured data further comprises generating a topographic height map of the label-free sperm cell. The generating of the topographic height map may comprise utilizing a refractive index map being characteristic of sperm cells.

In some embodiments, the measured data comprises a birefringence image data, and the processing of the measured data comprises generating a topographic birefringence map of the label-free sperm cell.

The at least one physical parameter comprises at least one of the following: head area; total volume of the head; width and length of the head; relative area or volume of the acrosome and nucleus within the head; total dry mass of the head; dry mass of the acrosome and nucleus; volume of vacuoles within the head, and their relative volume; centroid and weighted centroid of each head region and the distance between them; Mean OPD of each head region; variance or standard deviation of each head region; Mean anterior-posterior difference; midpiece width; midpiece length; tail length; presence of cytoplasmic droplets; tail form and head form.

In some embodiments, the data indicative of sperm quality for the label-free sperm cell comprises sperm fertility quality data.

In some embodiments, the data indicative of sperm quality for the label-free sperm cell comprises a quantitative quality score.

In some embodiments, the measured data is obtained for a plurality of label-free sperm cells, and a training data set is built comprising said at least one physical parameter for normal and abnormal sperm cells. The training data set may comprise data indicative of at least one of spatial, spectral and polarization state and birefringence distribution within a sperm cell. The sperm quality being indicative of a plurality of physical parameters is determined by comparing measured physical parameters with physical parameters of said training data set.

In some embodiments, the sperm quality is indicative of at least one of chromosomal aberrations within a nucleus of the cell, DNA fragmentation within the cell and sex of the sperm cell.

In some embodiments, the refractive index map is obtained by processing image data of at least one labeled sperm cell. The processing of the image data indicative of the at least one labeled sperm cell may comprise calculating a sperm refractive index map corresponding to different points in the labeled sperm cell, and generating and storing data indicative of a characteristic sperm refractive index map of said different points in the labeled sperm cell to thereby determine properties of a label-free sperm cell. The properties of a label-free sperm cell may comprise morphological parameters of the label-free sperm cell. The different points in the labeled sperm cell correspond to at least one of the following cellular compartments of the labeled sperm cell: vacuoles, in nucleus, acrosome, head, neck region and tail.

In some embodiments, the at least one labeled sperm cell is imaged to obtain the image data.

In some embodiments, the imaging of the labeled sperm cell is made with interferometric phase microscopy (IPM), while sequentially immersing said at least one labeled sperm cell in a first medium having a first refractive index and in a second medium having a second different refractive index, said image data comprising a first and second image data indicative of first and second phase map data, respectively.

In some embodiments, the imaging of the labeled sperm cell is made with interferometric phase microscopy (IPM), while immersing said at least one labeled sperm cell in a medium with a known refractive index and sequentially illuminating said at least one labeled sperm cell with light having first and second different light properties, said image data comprising first and second image data indicative of first and second phase map data, respectively. The light property comprises at least one of wavelength and polarization.

In some embodiments, the imaging of the labeled sperm cell is made with interferometric phase microscopy (IPM), while immersing said at least one labeled sperm cell in a medium with a known refractive index, said image data comprises a first image data indicative of a phase map data and a second image data indicative of physical thickness of said different points in the labeled sperm cell.

In some embodiments, the method comprises receiving and processing of the image data indicative of a plurality of labeled sperm cells, building a training data set comprising a plurality of sperm refractive index maps corresponding to the plurality of labeled sperm cells, and determining a characteristic sperm refractive index map from said plurality of the sperm refractive index maps. Said characteristic sperm refractive index map may be determined by averaging said plurality of sperm refractive index maps.

In some embodiments, the method comprises analyzing said topographical height map data and determining 3D morphology of the label-free sperm cell based on physical thickness distribution. The measured 3D morphology of the label-free sperm cell may be evaluated by correlating between it and theoretical data indicative of a computerized 3D morphology model of the label-free sperm cell. The computerized 3D morphology may be based on at least one characteristic dimension in an image of the label-free sperm cell. The measured data of the label-free sperm cell may comprise IPM data.

According to another broad aspect of the present invention, there is provided a method for use in sperm analysis, the method comprising processing image data indicative of at least one labeled sperm cell, calculating a sperm refractive index map corresponding to different points in the labeled sperm cell, generating and storing data indicative of a characteristic sperm refractive index map of said different points in the labeled sperm cell, to thereby determine properties of a label-free sperm cell.

According to yet another broad aspect of the present invention, there is provided a method for use in analysis of a biological organism, the method comprising imaging at least one labeled biological organism and obtaining image data, processing the image data and calculating a refractive index map corresponding to different points in the labeled biological organism, and generating and storing data indicative of a characteristic refractive index map and of said different points in the labeled biological organism to be used for determining properties of a label-free biological organism.

According to yet another broad aspect of the present invention, there is provided a computerized system for use in sperm analysis, the system comprising: a communication utility for receiving interferometric measured data of a sperm cell; and a processor utility configured and operable for processing said measured data and determining at least one physical parameter of said sperm cell, said processing comprising determining topographic optical phase delay (OPD) map of the label-free sperm cell, determining at least one physical parameter of the label-free sperm cell, and generating data indicative of a fertility quality score for the label-free sperm cell. In some embodiments, the processor utility is further configured and operable for utilizing the measured data and a characteristic refractive index map of a sperm cell, stored in a memory, calculating a physical thickness distribution of different points in said measured label-free sperm cell, and generating topographic height map for the label-free sperm cell.

In some embodiments, the system comprises a flow chamber configured and operable to trap said sperm cell and to allow imaging thereof. The processor utility may be configured and operable to control at least one of operation of said flow chamber, flow of the fluid inside the chamber, and substitution of different fluids for enhancing contrast of said sperm cell.

In some embodiments, the system comprises a memory utility configured and operable to store at least one of said measured data, results of analysis of the measured data, and characteristic refractive index map of said measured data.

According to yet another broad aspect of the invention, there is provided a device use in analysis and selection of cells, comprising a flow channel which comprises an inlet for receiving a fluid containing sperm cells, a selection zone downstream said inlet, and at least two outlets at said selection zone; and a flow driving mechanism comprising a flow driving unit configured and operable to generate a flow of said fluid containing sperm cells from said inlet towards at least first of said at least two outlets through said selection zone, and a collecting driving unit selectively operating along the direction of a second outlet of said at least two outlets to direct a portion of interest of said fluid containing sperm cells towards said second outlet.

According to yet another broad scope of the invention, there is provided a device for use in analysis and selection of cells, comprising a flow chamber comprising a microchannel configured and operable to allow applying analysis and imaging to a cell flowing in a medium thereinside, and two switchable gates at both sides of the micro-channel configured and operable to trap a single cell at a time inside said micro-channel. The device may further comprise a flow circuit configured and operable to substitute the medium inside said micro-channel while the cell thereinside, thereby enabling enhancing image contrast for specific organelles in the cell.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
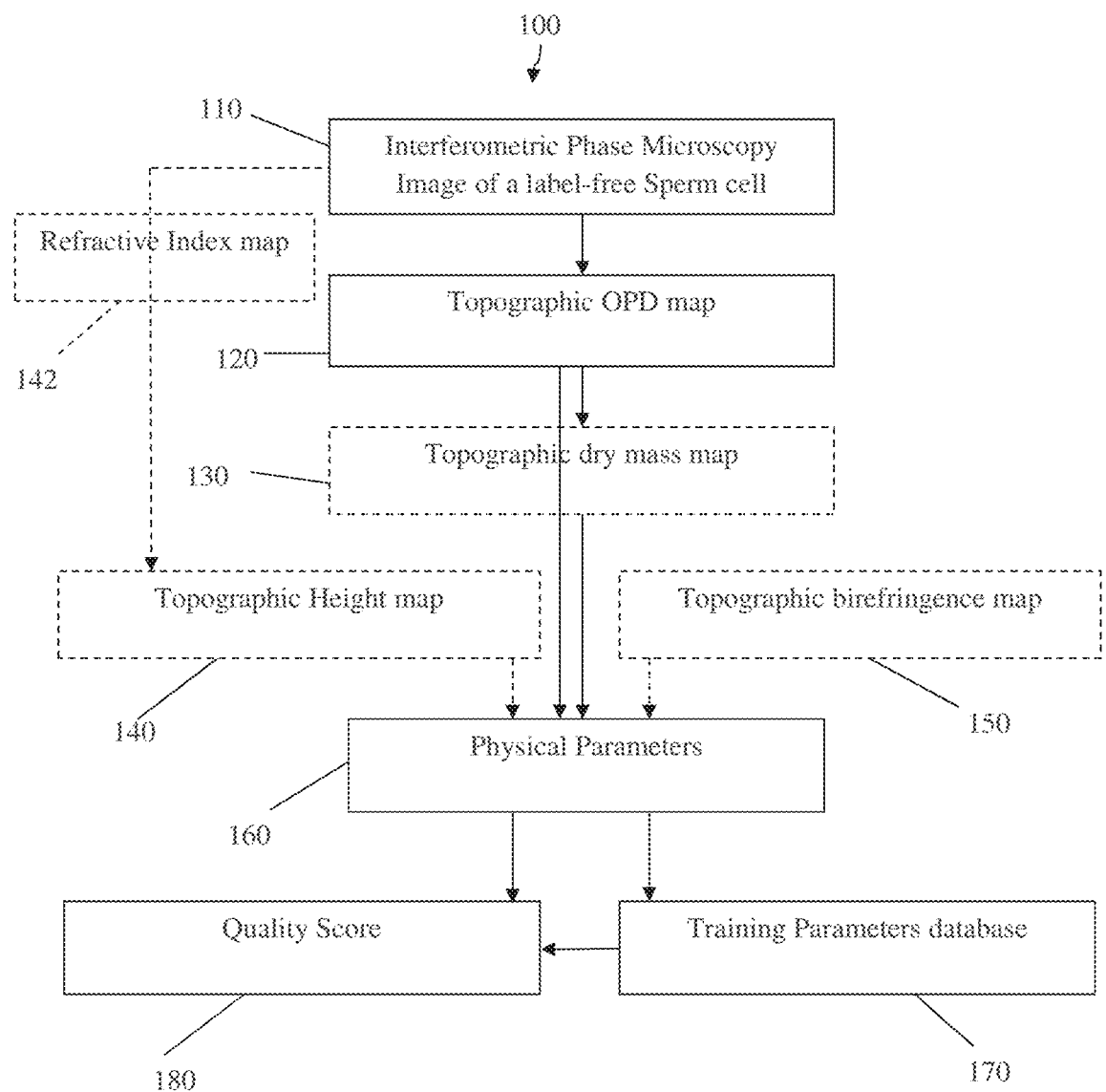
FIG. 1A illustrates a method for quantitative analysis according to one embodiment of the invention.

Reference is made to FIG. 1A exemplifying a flow diagram 100 of a method of the invention for in-vivo quantitative analysis of unlabeled, i.e. not stained, biological live cell/organism, such as a live sperm cell. The method may be used for effective and improved selection of a label-free sperm cell for intra cytoplasmic sperm injection (ICSI).

The method concerns quantitative IPM-based analysis of label-free sperm cells, taking into account at least the optical thickness (OPD) or the dry mass data of the sperm in all of its points. By utilizing these data, it is possible to evaluate a plurality of physical/morphological parameters of live sperm cells, such as the sperm head volume, neck volume and tail length. The method thus comprises processing images indicative of at least one label-free sperm cell and providing at least one of the optical thickness of the cell, the dry mass of the cell, the refractive index of the cell, the birefringence of the cell or a physical thickness of the cell in addition to its motility. The invention thus combines the ability of interferometric phase microscopy to provide non-invasive, label free imaging of several physical (morphological) parameters simultaneously.

In step 110, an IPM image of a label-free sperm cell is received. The imaging process itself is not part of the method 100, however, in some cases, especially when the examination of the sperm cell is done concurrently with the selection process, the system executing the method (such as the system 50 illustrated in FIG. 4) may comprise an IPM imaging facility. The image data in the digital era is typically a matrix of pixels that include digit values of the measured entity. In this case, the immediate measured entity by IPM is the optical phase delay (OPD) of the light passing through the sperm cell. Accordingly, the first data used for the acquisition of the physical parameters is the Topographic OPD map (step 120), which is a matrix in which the value of each pixel corresponds to the optical phase delay for that pixel.

In step 130 (dashed outline), a second map, the topographic dry mass map, is generated based on the OPD map 120. The topographic dry mass map 130 is a matrix in which the value of each pixel in the image corresponds to the dry mass within that pixel. The dry mass is calculated from the OPD as follows:

$$\sigma_{DM}(x, y) = \frac{OPD(x, y)}{\alpha}$$

-continued $$DM = \int\int_{Sc} \sigma_{DM}(x,y)dxdy = Sc \times \langle \sigma_{DM}(x,y) \rangle$$

Where Sc is the area of the pixel in the image, and $\langle\sigma_{DM}(x,y)\rangle$ is the average dry mass surface density over that area. α is the specific refractive increment in ml/g (0.18-0.21 ml/g).

Steps 140 and 150 (dashed outline) may be used for obtaining some of the physical (morphological) parameters, as will be further detailed below. Two additional maps may be generated as well: the topographic height map 140, in which the value of each pixel in the matrix corresponds to the thickness of the cell perpendicular to the optical axis, and the topographic birefringence map 150, in which the value of each pixel corresponds to the birefringence (in nm) of polarized light passing through the cell. The topographic height map 140 can be extracted from the OPD, if the refractive index 142 is known or estimated, as will be detailed below with reference to FIG. 2. In certain cases, a topographic height map 140 may be obtained by using an atomic force microscope to directly measure the physical thickness of dehydrated, fixated, un-labeled sperm cells.

Based on at least the OPD or dry mass topographic maps (dry mass or dry mass surface density can be used interchangeably herein), in step 160 the following physical parameters and/or morphological parameters may be obtained by using signal/image processing techniques, such as threshold, masks, moments and other known techniques:

Physical Parameters:
The head area (e.g. based on the actual number of pixels in the region);
The total volume of the cell head (the 2D integral of the height over the area of the cell);
The width and length of the head area;
The relative area (or volume) of the acrosome and nucleus within the cell head;
The total dry mass of the cell head;
The dry mass of different compartments (such as acrosome and nucleus) within the cell head;
The volume of vacuoles within the cell head, and their relative volume;
The centroid and weighted centroid of each head region is obtained and the distance between them is determined;
Mean OPD of each head region is determined;
Variance or standard deviation of each head region is determined;
Mean anterior-posterior difference=is the difference between the mean OPD values of the anterior and posterior halves of the sperm head. If there is no nucleus or no acrosome (or a very small acrosome) this value will be close to zero;
Perimeter: the total number of pixels around the boundary of each region in the image;
Analysis of 2D shape of the sperm head:
　Form factor: (4*pi*Area excluding holes)/(Perimeter*Perimeter); Equals 1 for a perfectly circular object;
　Roundness: (4*Area including holes)/pi*(Maximum diameter*Maximum diameter);
　Aspect ratio: (Major axis)/(Minor axis) or (width of head)/(length of head);
　Effective diameter: (Area including holes/pi)*2;
　Circular degree: pi*(Major axis)/4*(Area excluding holes);
　Circularity ratio: (4*pi*Area including holes)/(Perimeter*Perimeter);
　Thin degree: (Maximum diameter)/(Pattern width);
　Compact aspect ratio: ((4/pi)*(Area including holes)))$^{1/2}$/(Major axis);
　Elongation: (Perimeter*Perimeter)/(Area including holes);
　Roughness: (perimeter*perimeter)/(4*pi*(area excluding holes));
　Degree of circularity: 2*(pi*(Area including hole))$^{1/2}$/Perimeter
Relative position of head span:
　The relative distance of the position along the length of the head at which the width of the head is maximum=[(length of head)−(distance of point from posterior edge of head)]/(length of head)×100;
Longitudinal Asymmetry:
The measure of the longitudinal asymmetry of the head. This is done by dividing the head by an axis of symmetry drawn from the point at which the midpiece connects to the head, to the farthest point from this midpiece point located on a best-fit ellipse fitted to the head. The halves of the head are then overlaid by folding them along the axis of symmetry, the number of non-overlapping pixels is counted, and this number is subsequently divided by the total number of pixels in the head ("head area");
Anterior Area Distribution:
The head is compared to a perfect ellipse possessing the same length and width. This model ellipse is subtracted from the head image and the remaining number of pixels in the anterior half of the image is summed and divided by the area of the model;
Head non-ellipsity:
The anterior portion of the head is defined in this case as the anterior section of the two sections of the head after the head is divided into two parts along its length, using the point at which head width is at a maximum as the point of division. This anterior portion is mirrored in order to produce an elliptical region and a best-fit ellipse is found for this region. The image of the best fit ellipse is then subtracted from the head image, the values of the pixels is summed, and the result is divided by the head area;
Ellipse structural similarity index (SSIM):
The SSIM of the head is calculated by an elliptical mask possessing the same length and width as the head that is used as the reference image;
Anterior distension ratio:
Using the same method utilized in finding the head non-ellipsity, the head image is divided into two parts. The anterior part is mirrored along the line of division and subtracted from the posterior part. The number of negative pixels is then summed and divided by head area;
Posterior distension ratio:
Calculated using a process identical to that of anterior distension ratio, however in this case the number of positive pixels is summed and then divided by head area;
Net distension ratio:
　=(anterior distension ratio)−(posterior distension ratio)
Maximum value of normalized 2-D cross-correlation:
Using a predetermined number of images from of heads of cells possessing good head shapes as determined by a trained clinician, an average OPD image for good sperm heads is found and used as a template. The maximum value of normalized 2-D cross-correlation between the template and head image is then calculated.

Further, some parameters, obtained using image processing tools such as the software CellProfiler, can be obtained for the head and other parts of the sperm:

Solidity: The proportion of the pixels in the convex hull that are also in the object, i.e. ObjectArea/ConvexHullArea. Equals 1 for a solid object (i.e., one with no holes or has a concave boundary), or <1 for an object with holes or possessing a convex/irregular boundary;

Extent: The proportion of the pixels in the bounding box that are also in the region. Computed as the Area divided by the area of the bounding box;

EulerNumber: The number of objects in the region minus the number of holes in those objects, assuming 8-connectivity;

Center_X, Center_Y: The x- and y-coordinates of the point farthest away from any object edge;

Eccentricity: The eccentricity of the ellipse that has the same second-moments as the region. The eccentricity is the ratio of the distance between the foci of the ellipse and its major axis length. The value is between 0 and 1. (0 and 1 are degenerate cases; an ellipse whose eccentricity is 0 is actually a circle, while an ellipse whose eccentricity is 1 is a line segment);

MajorAxisLength: The length (in pixels) of the major axis of the ellipse that has the same normalized second central moments as the region;

MinorAxisLength: The length (in pixels) of the minor axis of the ellipse that has the same normalized second central moments as the region;

Orientation: The angle (in degrees ranging from −90 to 90 degrees) between the x-axis and the major axis of the ellipse that has the same second-moments as the region;

Compactness: The mean squared distance of the object's pixels from the centroid divided by the area. A filled circle will have a compactness of 1, with irregular objects or objects with holes having a value greater than 1;

MaximumRadius: The maximum distance of any pixel in the object to the closest pixel outside of the object. For skinny objects, this is ½ of the maximum width of the object;

MedianRadius: The median distance of any pixel in the object to the closest pixel outside of the object;

MeanRadius: The mean distance of any pixel in the object to the closest pixel outside of the object;

MinFeretDiameter, MaxFeretDiameter: The Feret diameter is the distance between two parallel lines tangent on either side of the object (imagine taking a caliper and measuring the object at various angles). The minimum and maximum Feret diameters are the smallest and largest possible diameters, rotating the calipers along all possible angles;

Zernike shape features: Measure shape by describing a binary object (or more precisely, a patch with background and an object in the center) in a basis of Zernike polynomials, using the coefficients as features (Boland et al., 1998);

FracAtD: Fraction of total stain in an object at a given radius;

MeanFrac: Mean fractional intensity at a given radius; calculated as fraction of total intensity normalized by fraction of pixels at a given radius;

RadialCV: Coefficient of variation of intensity within a ring, calculated over 8 slices;

Granularity;

TotalIntensity: Sum of all pixel intensity values;

MeanIntensity, MedianIntensity: Mean and median of pixel intensity values;

StdIntensity, MADIntensity: Standard deviation and median absolute deviation (MAD) of pixel intensity values. The MAD is defined as the median(|xi−median(x)|);

MinIntensity, MaxIntensity Minimum and maximum of pixel intensity values;

LowerQuartileIntensity: The intensity value of the pixel for which 25% of the pixels in the object have lower values;

UpperQuartileIntensity: The intensity value of the pixel for which 75% of the pixels in the object have lower values;

Texture:

a. Haralick Features: Haralick texture features are derived from the co-occurrence matrix, which contains information about how image intensities in pixels with a certain position in relation to each other occur together. The image is quantized into eight intensity levels. There are then 8×8 possible ways to categorize a pixel with its scale-neighbor. The 8×8 co-occurrence matrix is formed by counting how many pixels and neighbors have each of the 8×8 intensity combinations. Thirteen measurements are then calculated for the image by performing mathematical operations on the co-occurrence matrix:

b. AngularSecondMoment: Measure of image homogeneity. A higher value of this feature indicates that the intensity varies less in an image. Has a value of 1 for a uniform image.

c. Contrast: Measure of local variation in an image. A high contrast value indicates a high degree of local variation, and is 0 for a uniform image.

d. Correlation: Measure of linear dependency of intensity values in an image. For an image with large areas of similar intensities, correlation is much higher than for an image with noisier, uncorrelated intensities. Has a value of 1 or −1 for a perfectly positively or negatively correlated image.

e. Variance: Measure of the variation of image intensity values. For an image with uniform intensity, the texture variance would be zero.

f. InverseDifferenceMoment: Another feature to represent image contrast. Has a low value for inhomogeneous images, and a relatively higher value for homogeneous images.

g. SumAverage: The average of the normalized grayscale image in the spatial domain.

h. SumVariance: The variance of the normalized grayscale image in the spatial domain.

i. SumEntropy: A measure of randomness within an image.

j. Entropy: An indication of the complexity within an image. A complex image produces a high entropy value.

k. DifferenceVariance: The image variation in a normalized co-occurance matrix.

l. DifferenceEntropy: Another indication of the amount of randomness in an image.

m. Info Measure of correlation 1:

Formula:

$$\frac{HXY - HXY1}{\max\{HX, HY\}}$$

n. Info Measure of correlation 2:

Formula:

$$(1 - \exp[-2(HXY2 - HXY)])^{\frac{1}{2}}$$

where $HXY = -\Sigma_i \Sigma_j p(i,j) \log(p(i,j))$, HX, HY are the entropies of $p_z$ and $p_y$, $HXY1 = -\Sigma_i \Sigma_j p(i,j) \log \{p_x(i)p_y(j)\}$ $HXY2 = -\Sigma_i \Sigma_j p_x(i)p_y(j) \log \{p_x(i)p_y(j)\}$ In addition, all other parameters required by WHO for assessing sperm morphology can be determined from the IPM images, including, inter alia:
Midpiece width;
Midpiece length;
Tail length;
Presence of cytoplasmic droplets;
Tail form;
Head form.

According to the invention, a training database is created by imaging a cell with IPM and then defining "potent" and "impotent" (or normal and abnormal) cells based on clinical decision. One example for a method for clinically defining the potency for fertilization may include measuring all of the above parameters for sperm cells from many different male donors, and for specific sperm cells that are selected for fertilization by a clinician, recording if the fertilization was successful or not. Alternatively, an expert can define whether a cell is normal or abnormal based on clinical criteria, or on criteria defined by the WHO. Therefore, for each sperm imaged with IPM, a label "potent" or "impotent" (or normal and abnormal) will be attached to it. Then using statistical, multiparameter methods (such as ANOVA, clustering or any other method) a score that combines the statistically relevant parameters from the above list will be assigned to each configuration of measured parameters (or only to a selection of them).

Thus, in step 170, a training parameter database is built to obtain the physical parameters and/or their spatial, spectral or polarization distribution within a sperm cell for normal and abnormal cells. As appreciated and illustrated by the arrows in the figure, the training parameter database can include one or more of the following: OPD map, dray mass map, refractive index map, height map and polarization and birefringence map. The method of the present invention comprises evaluation of the images according to the morphological features of a cell and comparison of the outcome of the evaluation with a database of normal (e.g. potent) and abnormal (e.g. non-potent) cells. The computerized system of the present invention, as described herein below, can be used in sperm evaluation and selection for assistive reproduction techniques, such as IVF or ICSI. The database of normal and abnormal cells is built, in order to select the parameters that are used to provide a fertility quality score for the sperm cell.

As shown in step 180, the evaluation output may be a quantitative score that describes the potential of a given sperm to successfully fertilize an egg and produce a healthy offspring (potency). A "sperm quality score" that combines several of the physical parameters is created to evaluate sperm cells. For each new cell that is imaged using an interferometric phase microscope, a score is provided based on comparison of the measured parameters to those of the database. The comparison between the measured images to the database provides a score for the cell that reflects its potency for fertilization. This allows automatically informed screening of cells prior to selection for fertilization or for automatic diagnosis.

In some embodiments of the invention, the quality score is calculated based on the spatial distribution of a measured parameter (for example dry mass) within the cell. This spatial distribution can be calculated by the center of mass, the centroid of the cell, the skewness of the mass profile along a dimension of a cell or other parameters. Therefore, the spatial distribution of the measured parameters is a parameter for quality increasing the quality score of the sperm cell.

In yet other embodiments, the evaluation output is a quantitative score that describes chromosomal aberrations within the nucleus of the cell, such as Down's syndrome.

In yet another embodiment, the evaluation output is a quantitative score that describes DNA fragmentation within the cell.

It should be noted that, for example, the dry mass of the nucleus may be related to the amount of DNA within the nucleus. Variations in the amount of the nucleus weight indicate chromosomal aberrations or DNA fragmentation. It is known that fragmented DNA has a low chance of fertilization, thus by providing a "low score" to a sperm with abnormal dry mass (below or above a certain threshold), the technique of the present invention prevents selection of such cells for assisted reproduction. In addition, selection of cells without chromosomal aberrations reduces the occurrence of male caused genetic disorders in the offsprings, such as Down's syndrome, or death of the fetus. Another parameter that may be included in the score is the dry mass of the acrosome as well as its location and volume. As cells with a low acrosomal volume are also known to have DNA fragmentation, this additional information may be combined within the score. The polarization state or the birefringence distribution with a cell can also be used as a parameter.

In another embodiment of the invention, the evaluation output is a quantitative measure that relates to the sex of the sperm cell.

Figure 1B:
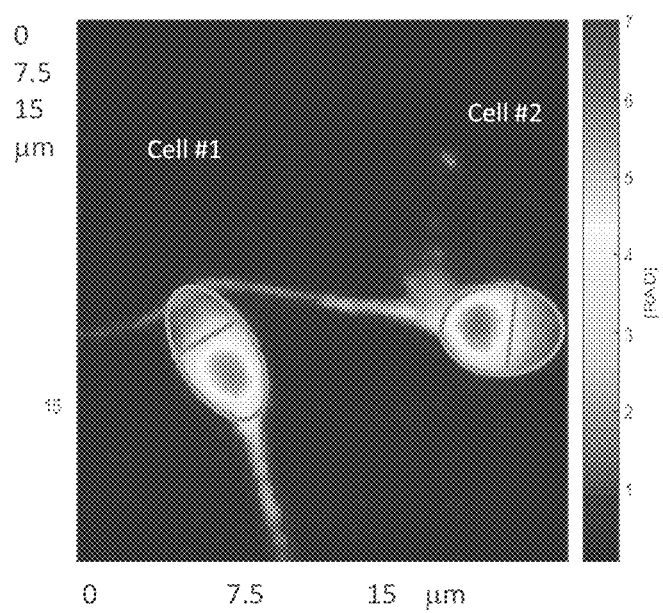
FIGS. 1B-1D illustrate some examples utilizing the method of the invention.
Figure 1C:
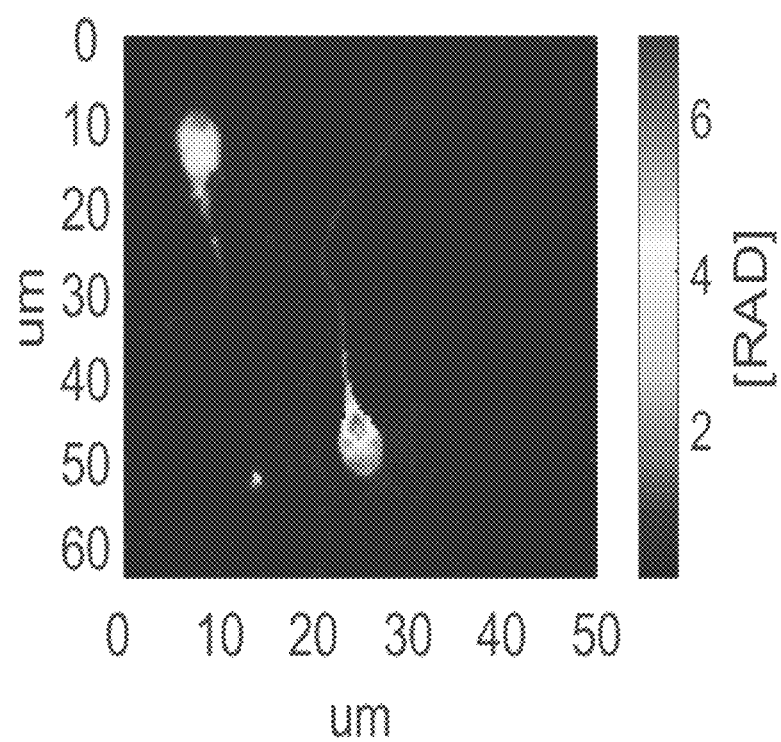
Figure 1D:
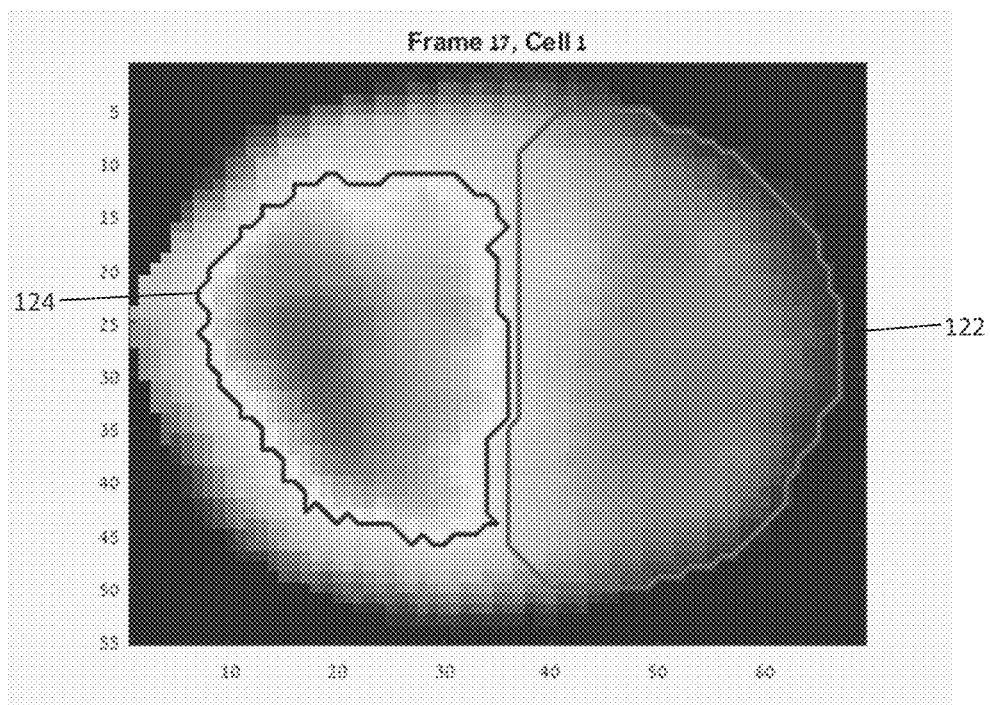

Reference is made to FIGS. 1B-1D and tables 1-4, showing experimental data for exemplary OPD maps and measured parameters for sperm cells imaged.

In FIG. 1B, an OPD map of two sperm cells #1 and #2 is presented and used, for example, to determine the head width, head length, head area, head volume, Acrosome area and its fraction, Acrosome volume and its fraction, dry mass of the head, the acrosome and the nucleus. The quantitative results are shown in Tables 1-3.

TABLE 1

| Cell # | Head Width (um) | Head Length (um) | Head area (um$^2$) | Volume (n = 1.35) (um$^3$) |
|---|---|---|---|---|
| 1 | 2.9 | 5.1 | 11.62 | 32.52 |
| 2 | 3.3 | 4.7 | 12.18 | 38.98 |

TABLE 2

| Cell # | Acrosome area (um²) | Acrosome Volume (n = 1.35) (um³) | Fractional area % | Fractional volume % |
|---|---|---|---|---|
| 1 | 4.40 | 1.32 | 38% | 4% |
| 2 | 5.70 | 1.37 | 47% | 4% |

TABLE 3

| Cell # | Dry mass of head (pgrams) | Dry mass of acrosome (pgrams) | Dry mass of nucleus |
|---|---|---|---|
| 1 | 6.8 | 1.3 | 5.5 |
| 2 | 7.2 | 1.1 | 6.1 |

All dry mass calculations used the following formula:

$$\text{drymass}[\mu g] = (\text{area}[\mu m^2]) \times \frac{\text{mean } OPD \text{ over area } [\mu m]}{1.8 \times 10^5 \left[\frac{\mu m^3}{\mu g}\right]}$$

The acrosome is identified in the area where the OPD per pixel is less then 300 nm (or another threshold value) for live cells in medium with a refractive index of 1.33. Therefore, the relative area of the pixels with an OPD lower than 300 nm (after filtering out the edges of the cells) may be calculated.

FIG. 1C exemplifies a sperm cell #3 with Vacuoles, the volume of vacuoles is calculated based on the radius inferred from the 2D image (assuming a sphere shape).

The values of the different physical parameters are shown in Table 4.

TABLE 4

| Cell # | Head area Volume (um³) | Acrosome Volume (um³) | Vacuoles Volume (um³) |
|---|---|---|---|
| 3 | 14.62 | 2.40 | 0.22 |

Based on all the volume measurements, a volume threshold for "potent" or "impotent" cell can be determined.

Additional analysis based on the topographic maps 120-150 may also include the following.

Determination of Anterior and Posterior Sides of the Cell's Head (Head Alignment):

In order to determine which side of each head region is the anterior side and which is the posterior side, the mask is compared to the original mask that was produced by applying the threshold or edge detection to the OPD map (specifically, the mask is obtained by applying a morphological opening filter using for example disk shaped structuring element with radius between 18-21 pixels, thus eliminating the pixels in the previously acquired "mask" that represent the tails of the sperm cells, as well as various other pixels that represent random noise or small artifacts and debris). By comparing matching regions from both masks and determining their respective centroid, the inventors can determine which side of the head region is which. This is due to the significant shift of the centroid from the center of the head in the current mask towards the tail still present in the original mask. Based on the elliptical shape of the head, the inventors can then determine precisely where the anterior and posterior sides of the head are.

Determination of Mean Anterior-Posterior Difference:

The difference between the mean OPD values of the posterior and anterior halves of the head is calculated by taking the mean of the OPD value of the posterior half and subtracting from it the mean OPD value of the anterior half. This value acts as a basic indicator of acrosome presence as well as nucleus presence.

Isolation of Acrosome and Nucleus:

Using a threshold defined, for example, as the average value of, for example 5, pixels with the highest OPD value in the head multiplied by, for example 0.6, the nucleus is determined and isolated from the rest of the head. Holes in the two different regions of the head that are comprised of 50 pixels or less are removed in order to facilitate proper isolation and measurement of nucleus and acrosome. In order to isolate the acrosome from the periphery of the head morphological opening is used with a disc shaped structuring element whose radius is determined by subtracting the width of the head without the periphery from the total width of the head and dividing by 2. The acrosome is then isolated by selecting the largest suitable region remaining on the anterior half of the head.

FIG. 1D exemplifies how the OPD map is used to determine by algorithm the borders 122 and 124 of the acrosome and nucleus respectively.

As mentioned above, the topographic height map 140 is used in order to obtain some of the physical parameters which are then used to generate the quality score of the sperm cell. The height map is the physical thickness of each point in the sperm cell, and can be calculated using the OPD map and a corresponding refractive indices map. Below, there are described various methods for acquiring the refractive index map and building a database of characteristic refractive index map to be used with the OPD data in order to give the physical thickness/height needed for calculation of several physical parameters.

Figure 2:
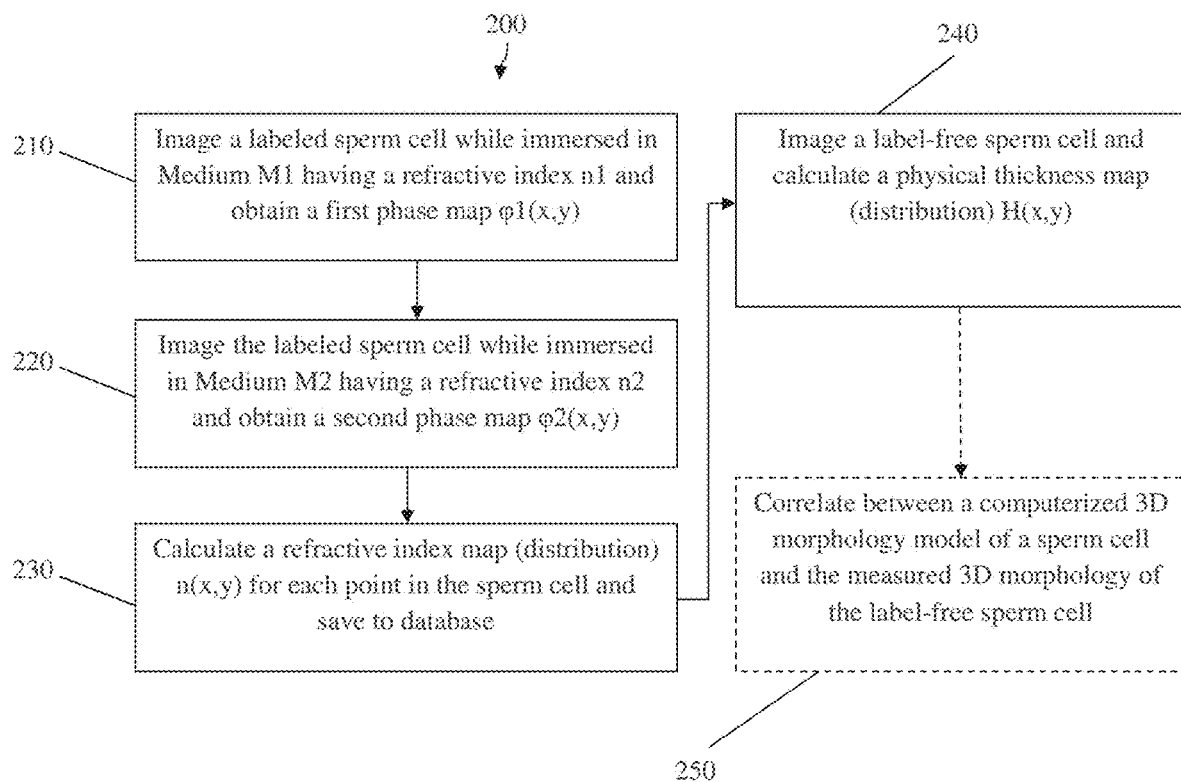
FIG. 2 illustrates a method for quantitative analysis according to a second embodiment of the invention, FIGS. 3A-3D exemplify embodiments of a device for using in sperm examination and selection procedure, according to one embodiment of the present invention, FIG. 3E exemplifies a flow chamber device for using in sperm examination and selection procedure, according to one embodiment of the invention.

Reference is made to FIG. 2 showing, in accordance with an embodiment of the present invention, a method 200 of quantitative analysis of unlabeled biological cell/organism, such as a sperm cell, by utilizing the topographic height map (i.e., the physical thickness). It should be noted that in some embodiments, the method can utilize the topographic OPD map or the dry mass map in addition or instead of the topographic height map. The method may be used for effective and improved selection of a label-free sperm cell for intra cytoplasmic sperm injection (ICSI).

The method concerns quantitative IPM-based analysis of label-free sperm cells, taking into account the physical thickness of the sperm in all of its points. The method includes generating a characteristic refractive index map (e.g. refractive index distribution along the sperm cell) determined on labeled sperm cell(s) (e.g. training set), and use of the characteristic refractive index map for analysis of label-free sperm cells. More specifically, the characteristic refractive index map may then be used to calculate the real physical thickness of each point of any label-free sperm cell by only using a measured phase map of the label-free sperm cell (e.g. by acquiring an interferometric image of the label-free sperm cell). For determining the characteristic refractive index map, generally at least one labeled sperm cell can be used, or a training set of a plurality of labeled sperm cells can be used and data indicative of the plurality of the cells is processed, e.g. averaged. Additionally or alternatively, a characteristic OPD map, a characteristic dry mass map or a characteristic birefringence map can be generated from suitable measurements, as described above, on the one or more labeled sperm cell(s) to be saved in a training data set and used as needed in the examination of a label-free sperm cell. In the example of FIG. 2, the method is described in relation to calculating the characteristic refractive index map, however this should not be interpreted as limiting the invention. Any combination of the maps may also be used for the analysis.

The refractive index map, and consequently the characteristic refractive index map, may be acquired by utilizing different methods, as will be detailed below.

A first non-limiting example of a method for obtaining the refractive index map is illustrated in steps 210 and 220 of FIG. 2. In the first step 210, a labeled sperm cell is immersed in a medium M1 having a known refractive index $n_1$ and imaged (e.g. using an interferometric system) to obtain phase data corresponding to optical thickness map. The complex wave front of the phase interference is recorded and an optical thickness map is acquired. The optical thickness is a function of the real physical thickness and the refractive index. The equation which describes this relation in this specific scenario is:

$$\varphi_1(x,y) = 2\pi/\lambda \cdot h(x,y) \cdot (n(x,y) - n_1);$$

where $\varphi_1(x,y)$ is the optical thickness recorded; $\lambda$ is the light wavelength, $h(x,y)$ is the physical thickness of the sperm cell and $n(x,y)$ is the distribution of the sperm cell refractive indices in every point in the 2-D image.

As appreciated, if the labeled sperm cell is irradiated with light of the same light property(ies) (e.g. a single wavelength, and/or the same polarization state), this equation has two unknowns $h(x,y)$ and $n(x,y)$. In order to find the values of the unknowns, the labeled sperm cell is immersed in a second medium M2 (second step 220) having a refractive index $n_2$ and imaged to capture the optical thickness map (phase map) $(p_2(x,y))$, where:

$$\varphi_2(x,y) = 2\pi/\lambda \cdot h(x,y) \cdot (n(x,y) - n_2).$$

Then, the unknowns $h(x,y)$ and $n(x,y)$ can be found for each point (x, y) in the imaged sperm.

Alternatively and equally effective, instead of immersing the labeled sperm cell in two mediums having two known refractive indices, a second method for obtaining the refractive index map may include immersing the labeled sperm cell in one medium with a known refractive index $n_0$, and irradiating the labeled sperm cell twice, each time with light of different light properties, such as a different wavelengths or different polarizations, provided that the sample refractive index has a large/strong dependency in this specific light property. In this example, use of different wavelengths is considered. As appreciated, the unknowns are still $h(x,y)$ and $n(x,y)$, which can be found from the following set of equations:

$$\varphi_1(x,y) = 2\pi/\lambda_1 \cdot h(x,y) \cdot (n(x,y,\lambda_1) - n_0);$$

$$\varphi_2(x,y) = 2\pi/\lambda_2 \cdot h(x,y) \cdot (n(x,y,\lambda_2) - n_0).$$

When using the second method of changing the wavelength of the light, the two wavelengths may be in the close UV, where the dependency of $n(x,y)$ and $\lambda$ is strong. Alternatively, adding a dye to the medium may enhance the measurement so that $n_0$ will be strongly dependent on the wavelength.

A third non-limiting example of a method for obtaining the refractive index map is to utilize imaging of the labeled sperm cell by IPM with light of known optical properties, e.g. wavelength $\lambda_0$, while the cell is immersed in a medium having a known refractive index $n_0$, and obtaining data about the physical thickness $h(x,y)$ using a system that can measure the physical thickness of the cell. Measuring physical thickness can be done by several known systems, such as Atomic Force Microscopy (AFM), Confocal Microscopy or Reflection interferometry. In this method, the only unknown in the equation $\varphi(x,y) = 2\pi/\lambda_0 \cdot h(x,y) \cdot (n(x,y) - n_0)$ is the refractive index map $n(x,y)$ (since $h(x,y)$ is measured by another method), so it can be easily calculated.

In step 230, data indicative of the refractive index map of the labeled sperm cell is recorded as a characteristic refractive index map, and stored in a storage utility (database) to be accessed and used when measuring on label-free sperm samples. It is assumed that the refractive indices of the different organelles in the sperm cell have constant values in every sperm cell. Steps 210 and 220 are performed using a labeled sperm cell in order to define the transverse locations of the different organelles in the cell and correlate between the location of the different organelles and the distribution of the calculated refractive indices $n(x,y)$, such that each refractive index $n(x,y)$ in the map/distribution corresponds to a specific organelle in the sperm cell.

In step 240, an unlabeled (label-free) sperm cell is measured. To this end, the unlabeled sperm cell may be immersed in a medium M of a known refractive index n (e.g. n1), is imaged with IPM, and an optical phase map $\varphi(x,y)$ is measured. Similar to the above equations, the acquired optical phase map $\varphi(x,y)$ is related to the real physical thickness $h(x,y)$ of the sperm cell and the refractive index map $n(x,y)$, as follows:

$$\varphi(x,y) = 2\pi/\lambda \cdot h(x,y) \cdot (n(x,y) - n).$$

The refractive index map, $n(x,y)$, is previously determined as described above and stored in the memory. The only one unknown in the equation is $h(x,y)$, which thus can be calculated for every location $(x1,y1)$ of a specific organelle, according to the $n(x1,y1)$ value corresponding to the specific organelle, as was found. In other words, the thickness/height of every organelle in the label-free sperm cell can be calculated.

The so-obtained physical thickness distribution/map can then be used to obtain measured 3D morphology of the label-free sperm cell.

This thickness map data can for example be used to assess the sperm cell and its suitability for different clinical procedures, such as ICSI procedure.

Further, as shown in FIG. 2, additional quantitative analysis and image processing may be performed on the obtained phase image of the sperm cell. In step 250 (optional), dimensions in the XY plane (transverse locations) in an acquired image of an organelle in the sperm cell can be combined with previously known morphological data, e.g. literature data, about the organelle in order to generate a three-dimensional computerized model of the organelle. This computerized 3D model of the organelle may be compared to the measured 3D morphological shape of the organelle that was obtained by the IPM measurements as described above, i.e. the physical thickness map of the specific organelle. This comparison may teach about the functionality of the sperm cell during an examination for IVF and ICSI procedures.

For example, the sperm cell neck may be examined. It is known that the neck of a sperm cell is cylindrical. By calculating the width W of the neck in XY plane in an acquired IPM image (for simplicity, if it is supposed that the sperm is aligned along the x axis with length X, then the neck width W is along the y axis), this width W is practically the transverse diameter of the cylindrical neck along the y axis. Supposing a perfect cylinder, then the physical depth along z axis should also be equal to W. A computerized cylindrical form of a diameter W and a length X can be constructed using specialized software. On the other side, the real 3D shape of the neck can be also formed by using the measured thickness map H(x,y). The computerized cylindrical form (3D model) and the measured 3D shape of the neck can be correlated and compared, using fitting software, in order to determine the healthiness of the sperm cell.

According to the invention, another diagnostic technique for the label-free sperm cell is based on creation of increased image contrast from sperm organelles, e.g. vacuoles, without labeling. Since different organelles have different refractive indices, by immersing the sperm cell in a medium of appropriate refractive index, it is possible to enhance the contrast for a specific organelle during imaging with IPM which would otherwise not provide desired image contrast. As a non-limiting example, it is known that the refractive index of the vacuoles is significantly lower than the refractive index of the other cellular contents. If the sperm cell is immersed in a medium having a refractive index higher than the refractive index of the vacuoles (plus the cellular material located above and below the vacuoles), the contrast in the vacuole location will be inverted and enhanced. In order to control contrast and induce distinctive contrast from the vacuole location, the sperm cell is immersed in a medium with a higher refractive index as compared to that of vacuole location. Thus, generally, the medium for immersing the sample therein for IPM measurements should preferably have a refractive index higher than at least that of the cell components having relatively low refractive index.

Figure 3D:
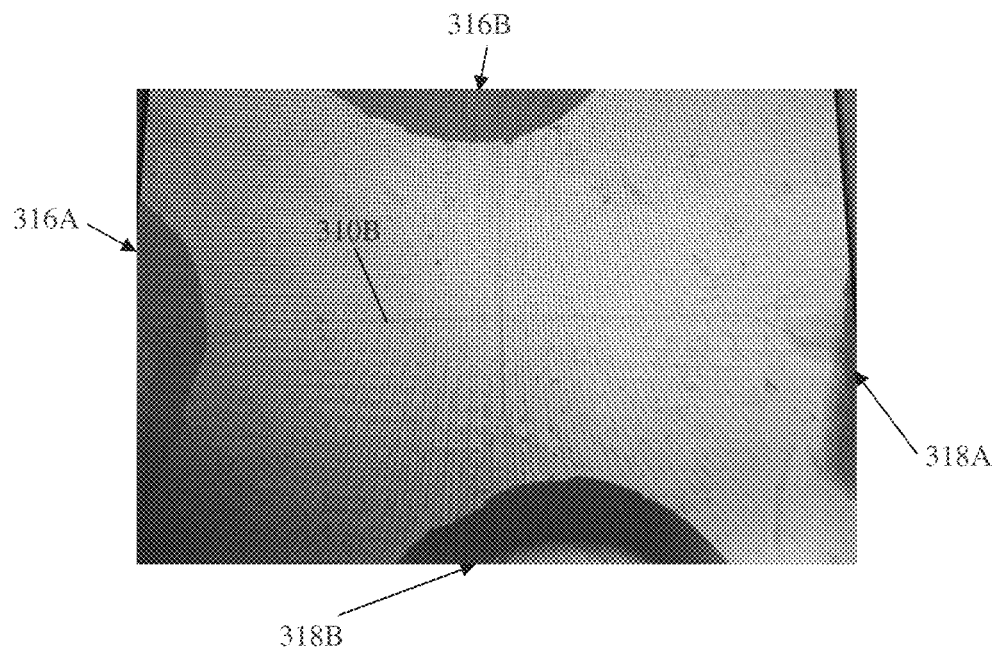
Figure 3D:
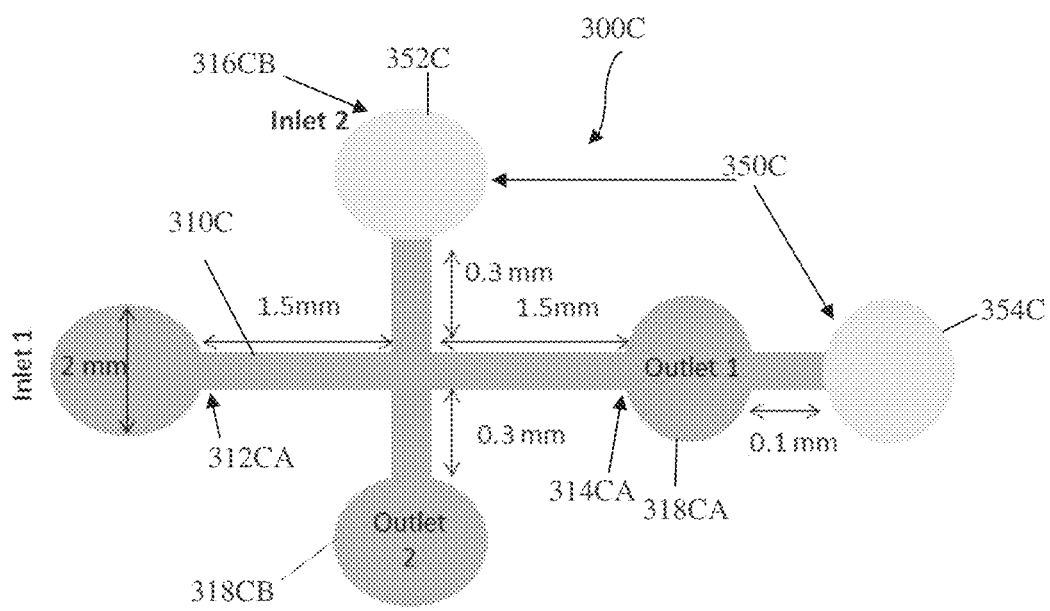
Figure 3E:
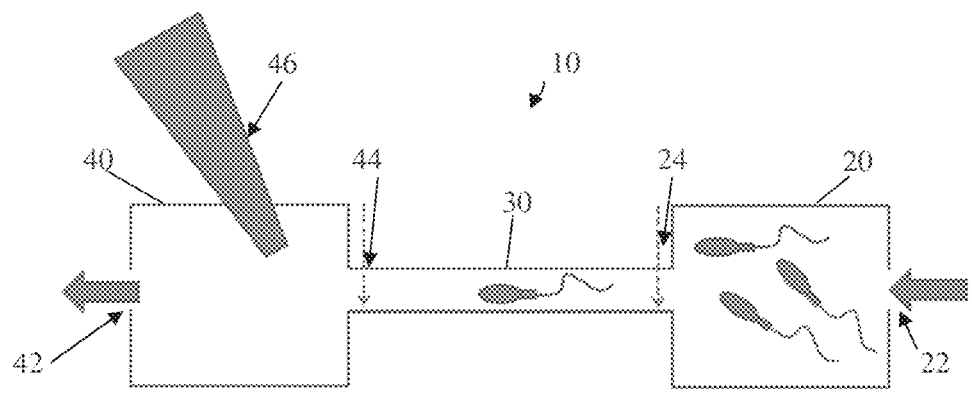

Reference is now made to FIGS. 3A-3E, illustrating non-limiting examples of a device for analysis and selection of single cells/sperm cells, in accordance with the invention. In all the figures, the device for analysis and selection of cells utilizes a cell-by-cell analysis (examination and classification) and selection (sorting), by including a micro-fluidic channel/chamber, in which a single cell is allowed to flow across the channel at each given time, while a plurality of cells undergoing analysis and selection can flow along the micro-channel. FIGS. 3A-3D give examples of the sorting part while FIG. 3E gives an example of the analysis part of the device.

In FIG. 3A, a non-limiting embodiment of a device for analysis and selection of cells is presented. As shown, the device 300 includes a channel 310 which has an inlet 312 and two outlets 314A and 314B. The channel 310 is configured as a micro-fluidic channel with dimensions that allow a single cell to flow through the channel at each given time. Examples for the dimensions suitable for specific applications, such as for sorting of the human sperm cells, are illustrated below.

Each inlet or outlet can be connected to and in fluid communication with a respective port being configured to receive a relatively large amount of cells before and after the sorting process. In some embodiments, as will be shown further below, the ports can be integrated with the micro-fluidic channel.

It should be noted that the number of channels in the device can be more than one. The number of inlets/inlet ports and outlets/outlet ports can be more than one and two respectively. This enables, when desirable, increasing the output by including a plurality of channels and/or outlets. For example, an optional second inlet 312B and an optional third outlet 314C are shown (with dashed lines). In case more than one inlet is provided, as will be further described below, the additional inlet(s) are usually used to inject into the device fluid rather than cells which undergo examination and selection.

As shown, the device 300 also includes an analysis zone 320 located after the inlet(s) 312, and a selection zone 330 located after the analysis zone 320 and before the outlets 314A and 314B. In some embodiments, the device also includes an intermediate zone 340, located between the analysis and selection zones. The intermediate zone 340 can be necessary/useful where the classification and decision making stage about the cells lasts for a period of time while the cells keep flowing inside the channel towards the selection zone. An analysis unit/utility 322 is located in the analysis zone 320 and configured for examining the cell and characterizing it so to classify the cell as chosen (suitable) or unchosen (not suitable). Such an analysis unit/utility can be an IPM system utilizing the technique described above, as will be further illustrated in FIG. 4.

The device 300 also includes a flow driving mechanism 350 which is configured to cause and/or affect movement (by deflecting/changing the propagation direction) of the cells inside the channel 310. The flow driving mechanism 350 can include one or more driving units 352 configured to cause or affect the flow and/or the movement of the cells inside the channel.

In one embodiment, the flow driving mechanism 350 includes a collecting driving unit 352 located in the selection zone 330 or acting on cells when in the selection zone 330. In this case, the collecting driving unit 352 acts only to affect flow and/or the movement of the cell, when it is inside the selection zone 330, towards one of the outlet ports 314A and 314B, based on the classification made during/after the examination stage in the analysis zone 320. In some embodiments, the collecting driving unit 352 is activated to act only on the chosen cells, by affecting only their movement towards one of the outlets. In some other embodiments, the collecting driving unit 352 is activated to act only on the unchosen cells, by affecting only their movement towards one of the outlets. In yet some other embodiments, the collecting driving unit 352 is activated to act on both the chosen and unchosen cells to direct movement of each cell to its relevant/dedicated outlet.

In a second embodiment, the flow driving mechanism 350 further includes a flow driving unit 354 configured to cause the movement of the cells inside the micro-fluidic channel 310. The flow driving unit 354 acts all the time on the cells when they enter and pass through the whole length of the channel 310, between the inlet 312 and the outlets 314A and 314B, or at least during the time when the cells are inside the analysis zone 320 and the optional intermediate zone 340, whereas the movement inside the selection zone 330 is driven by the collecting driving unit 352 only. In one example, the flow driving unit 354 can be configured to generate a steady flow of fluid, and consequently a steady flow of cells inside the fluid, along the channel 310 from the inlet port towards one of the outlet ports, while the collecting driving unit 352 acts in the selection zone 330, in addition to the flow driving unit 354, to further affect the movement of the chosen and/or unchosen cells when they pass inside the selection zone 330, to thereby enable selectively collecting them through one or more than one of the outlet ports. In the latter case, the flow driving unit 354 may be called also a constant or primary driving unit, and the collecting driving unit 352 may be called a temporary or secondary driving unit.

In the following, several examples of the device 300 are presented. Specifically, the examples differ from each other in the selection zone/sorting utility, while they share the same structure of the analysis and optional intermediate zones. It should be understood that while the description below emphasizes the sorting/selection utility of the device, the analysis utility can be configured according to the examination of cells described above in the present invention or according to any examination technique known in the art. Some of these examples are shown schematically as well as in their fabricated designs which have been fabricated by the inventors. The fabrication of these designs have been done using polydimethylsiloxane (PDMS), being one of the preferred materials for the fabrication of microfluidic devices due to its mechanical, chemical and thermal stability, ease of fabrication and low cost of fabrication. More details on the fabrication process are outlined herein further below.

Figure 4:
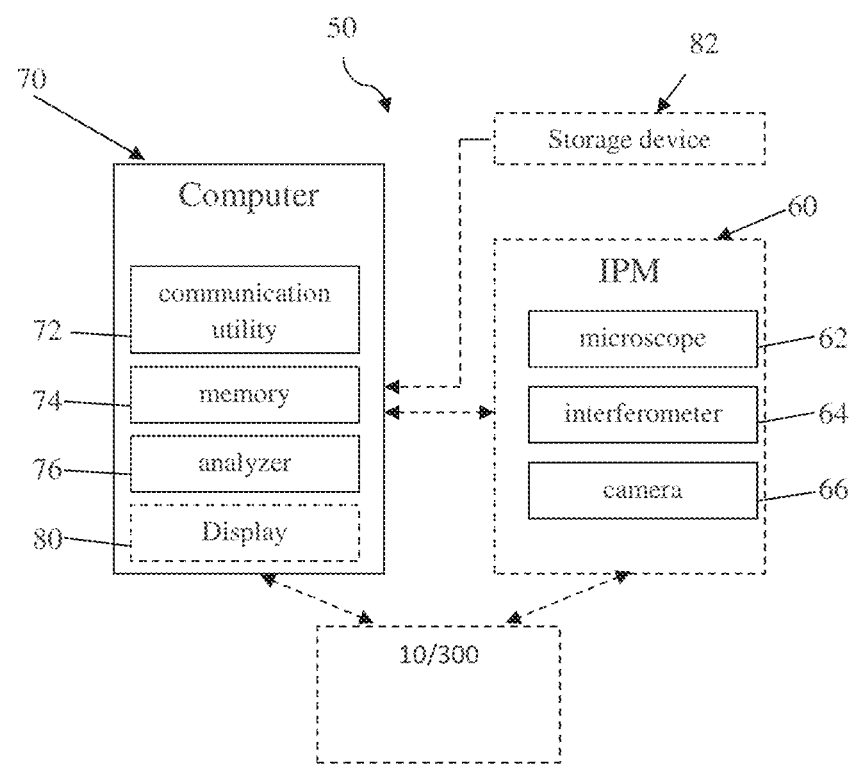
FIG. 4 illustrates an example of a system according to one embodiment of the present invention.

Reference is made to FIGS. 3B1-3B4, showing a non-limiting example of the device 300A for analysis and sorting of cells, such as human sperm cells, in accordance with the present invention. It should be noted that components having the same or similar function as described above with reference to FIG. 3A, are numbered with the same numbers with a suffix letter. For example, 310A is a channel having the same function as the channel 310, etc. FIG. 3B1 is a view from above on the device 300A. FIG. 3B2 is a view of a cross section made along the line A-A. As shown, the device 300A includes a micro-fluidic device/channel 310A, having one inlet 312A and two outlets 314AA and 314AB. In this example, the micro-fluidic channel includes an integral inlet port 316 connected to the inlet 312A and two integral outlet ports 318A and 318B connected respectively to the outlets 314AA and 314AB. The micro-fluidic channel has a "T" or T-like shape configuration (T-like shape includes a "Y" shape, such that the angles between the three different arms are not restricted to 90°), in which cells that are chosen/unchosen are driven to exit the channel through the outlet port 314AB, while the rest, unchosen/chosen cells respectively, leave the channel through the outlet 314AA. In this specific example, all of the inlet and outlet ports have cylindrical shapes having a diameter of 2 mm as shown, and a sufficient height of typically several millimeters to enable effective injection and collection of the cells into the inlet port and from the outlet port respectively, e.g. by using a pipette (not shown). The channel's width is chosen according to the cells being examined and/or sorted, such that only one cell can flow through the channel at a given time. The channel's length influences the time of the selection process, such that a shorter channel decreases the time of the process while a longer channel can be required to enable completing the analysis phase and generating the classification decision before sorting. In the shown example, the width and total length of the microchannel 310A are 12 μm and 3 mm respectively. The second outlet 314AB is located half-way between the inlet 312A and the first outlet 314AA. The height of the microchannel, as shown in the cross section view in FIG. 3B2 is 7 μm, suitable for sperm cells. Sperm cells that are cleaned from the semen using, for example, the swim up method or gradient centrifugation, are inserted to the inlet port 316 using a pipette.

In the described example, the device 300A includes a flow driving mechanism 350A which includes a primary driving unit 354A (the flow driving unit) and a secondary driving unit 352A (the collecting driving unit). The two driving units 352A and 354A are configured as two computer controlled syringe pumps connected to the two outlet ports 318B and 318A respectively. The syringe pump 354A is always active, with a flow rate of 5 μl/hr, and configured to cause the steady fluid flowing and or steady movement of the cells inside the channel between the inlet 312A and the outlet 314AA. The syringe pump 352A is selectively activated when a chosen/normal cell is detected during the analysis phase. The flow rate of the syringe pump 352A is chosen to be much higher than the constantly active syringe pump 354A, such that it deflects the chosen sperm cell, from the general flow propagation direction towards outlet 314AA, by pulling the chosen sperm cells towards the outlet 314AB. For example, the pump 352A is activated each time for one second with a flow rate of 300 μl/hr.

It should be understood that the pumps, acting as the flow driving units/collecting driving units, can be integral with or built in the respective inlet or inlet. Alternatively, the pumps can be located in the vicinity of, e.g. attached to, the respective inlet/outlet. When located in the vicinity, the pump(s) can be positioned inside or outside the respective inlet/outlet. In some embodiments, part of the pumps can be integrated in the respective inlet/outlet, while the other part can be located in the vicinity of the respective inlet/outlet.

FIG. 3B3 is a microscopic image of the fabricated microfluidic channel 310A with the integrated inlet port 316 and outlet ports 318A and 318B. FIG. 3B4 shows a higher-magnification microscopic image of the fabricated microfluidic channel 310A, the outlet 314AB and the outlet port 318B.

Reference is made to FIGS. 3C1-3C2, showing a non-limiting example of the device 300B for analysis and sorting of cells, such as human sperm cells, in accordance with the present invention. It should be noted that components having the same or similar function as described above with reference to FIG. 3A, are numbered with the same numbers with a suffix letter. For example, 310B is a channel having the same function as the channel 310, etc. FIG. 3C1 is a view from above on the device 300B.

As shown, the device 300B includes a micro-fluidic device/channel 310B, having two inlets 312BA and 312BB and two outlets 314BA and 314BB. The micro-fluidic channel has a "cross" or cross-like shape configuration, in which cells that are chosen/unchosen are driven to exit the channel through the outlet port 314BA, while the rest, unchosen/chosen cells respectively, leave the channel through the outlet 314BB. The inlets are integrally connected to inlet ports 316A and 316B and the outlets are integrally connected to outlet ports 318BA and 318BB. All the ports have cylindrical shapes having a diameter of 2 mm as shown, and height of, typically several millimeters, to enable effective injection and collection of the cells, e.g. by using a pipette (not shown). The width and total length of the microchannel 310B can be similar to that of microchannel 310A, e.g. 12 μm and 3 mm respectively. The second outlet 314BB is located half-way between the first inlet 312BA and the first outlet 314BA, and against (opposite) the second inlet 312BB. Sperm cells that are cleaned from the semen using, for example, the swim up method or gradient centrifugation, are inserted to the first inlet port 312BA. No cells are inserted through the second inlet port 312BB.

One of the differences between the example described in FIGS. 3B1-3B4 and the example described in FIG. 3C1-3C2 is in the sorting utility and the flow driving mechanism 350B. Specifically, in this example, the device 300B includes a flow driving mechanism 350B which includes a primary driving unit 354B (the flow driving unit) and two secondary driving units 352BA and 352BB (both forming the collecting driving unit). The three driving units 352BB, 352BA and 354B are configured as computer controlled syringe pumps connected to the second inlet port 316B and the outlet ports 318BA and 318BB respectively. The syringe pump 354B is always active, and configured to cause the steady flowing movement of the cells inside the channel between the inlet 312BA and the outlet 314BA. The syringe pumps 352BA and 352BB are activated only when a chosen/normal cell is detected during the analysis phase. The syringe pump 352BA applies a withdrawal pressure (pull) and the syringe pump 352BB applies an infusion pressure (push) to the sperm in the field of view at the center of the cross. The withdrawal-infusion pressure pushes the chosen sperm cell effectively into outlet port 318BB. The flow rate resulting from activating the two pumps 352BA and 352BB is chosen to be much higher than flow driven by the constantly active syringe pump 354B, such that this difference in flow rate deflects the chosen sperm cell, from the general flow propagation direction towards outlet port 318BA, towards the outlet 318BB. In this example, the pressure applied by each of the two pumps 352BA and 352BB is lower than the pressure applied by the single pump 352A, while its effect, when the three pumps are acting concurrently, is much higher.

FIG. 3C2 is a microscopic image of the fabricated microfluidic channel showing the channel 310B and portions of the integrated inlet and outlet ports.

Referring to FIG. 3D, there is illustrated another non-limiting example of a device 300C for analysis and sorting of cells, such as human sperm cells, in accordance with the present invention. It should be noted that components having the same or similar function as described above with reference to FIG. 3A, are numbered with the same numbers with a suffix letter. For example, 310C is a channel having the same function as the channel 310, etc.

The channel 310C has a cross shape configuration like the channel 310B, with two inlets and two outlets, such that the inlet in which the cells are injected is opposite to the outlet where the cells which are not diverted exit the channel, and the inlet which does not receive cells therein is opposite the outlet where the cells which are diverted exit the channel.

The device 300C is an example of a lab-on-chip microfluidic device having an integrated flow driving mechanism 350C. The flow driving mechanism 350C includes two micro-pumps 354C and 352C integrated in the chip. The first micro-pump 354C (the flow driving unit) is connected to the first outlet port 318CA and is constantly active in withdrawal pressure mode to pull fluid and cause movement of the cells inside the channel 310C between the inlet 312CA and outlet 314CA. The second micro-pump 352C (the collecting driving unit) is connected to the second inlet port 316CB and is selectively activated in infusion pressure mode to push chosen cells towards the outlet port 318CB.

Referring to FIG. 3E, there is provided an embodiment of a non-limiting example of a device used for inducing contrast from various organelles in cells in general, and in sperm cells in particular, while the cells are being imaged. As such, the device 10 illustrates a non-limiting example of an analysis procedure in the analysis zone. A flow chamber 10 includes an inlet container 20, an outlet container 40 and a micro-channel 30 between them. Two switchable membrane gates 24 and 44, separate between the inlet container 20 and the micro-channel 30 and between the micro-channel 30 and the outlet container 40, respectively. Plurality of sperm cells is entered into the inlet container 20 through an inlet 22. At a time, one sperm cell flows into the micro-channel 30 and the switchable gate 24 closes such that the sperm cell is trapped and no other sperm cell exists in the micro-channel. The switchable gate 44 is also closed at this time to prevent the sperm cell from exiting the micro-channel 30. When in the micro-channel 30, the sperm cell is imaged by any method or means desired, specifically by IPM. The switchable membrane gates 24 and 44 are permissible to medium flow but not to cells. The medium through the whole flow chamber can thus be altered and substituted (i.e. the refractive index of the medium is changed) in order to enhance contrast for specific organelles in the cell, according to the description above. Alternatively, the medium may be changed only inside the micro-channel 30, through a flow circuit connected only to it (not shown); in this case, the switchable gates 24 and 44 are preferably not permissible to any flow through them.

The same sperm cell may be imaged several times inside the micro-channel 30, each time while surrounded by a different medium enhancing a different organelle of the sperm cell. If the sperm cell is label-free, it can be tested for ICSI eligibility. The flow chamber 10 may be used to image the sperm cell for real time 3D morphology evaluation as described earlier. After finishing with imaging, the switchable membrane gate 44 is opened (while the switchable membrane gate 24 is closed), and the sperm cell moves into the outlet container 40. Based on the real-time analysis of the sperm cell, it may be selected to flow through the exit 46, if it is chosen for ICSI or any relevant procedure, or otherwise flow through the exit 42 as not suitable for the procedure. The selection stage can be performed by utilizing any of the flow driving mechanisms described above with reference to FIGS. 3A-3D.

As can been seen in FIGS. 3B3, 3B4 and 3C2, the inventors have fabricated the device of the invention using polydimethylsiloxane (PDMS). The advantages such as the ease of fabrication, mechanical, chemical and thermal stability and low cost of fabrication make PDMS one of the most preferred materials for the fabrication of microfluidic devices. In the following, a description of the fabrication process is given.

This specific device fabrication mainly consisted of two steps: fabrication of SU-8 master mold using photolithography, and fabrication of PDMS microfluidic devices using soft lithography.

Initially, the desired design of the device was modeled using Clewin, a layout editor software. The design was then transferred to a chromium coated photomask using laser lithography. The laser exposure was performed using a laser lithographic unit, which is equipped with a diode laser source that emits at a wavelength of 405 nm. Subsequently, using photolithography the pattern on the photomask was transferred to SU-8 coated silicon substrate to prepare the master mold. Primarily, silicon wafer was cleaned using isopropanol and dried at 100° C. for 30 min. on a hot plate. Cleaned silicon wafer was then coated with SU-8 3050, an epoxy-based negative photoresist, by spin coating at a spinning speed of 3500 rpm for 30 s. To remove the excess solvent, SU-8 coated silicon wafer was then soft baked at 95° C. for 3 min. on a hot plate. Soft bake was followed by UV exposure of the soft baked wafer with an exposure dose of 150 mJ/cm2 through the photomask using a mask aligner. In order to thermally cross link the exposed area of the photoresist, the wafer was then post baked at 95° C. for min on a hot plate. The post baked wafer was then developed using 1-Methoxy-2-propyl acetate (PGMEA) for about 3 min. and air dried. Finally, to improve the mechanical stability, the developed sample was hard baked at 95° C. for 20 min. on a hot plate. Direct bonding of PDMS to the SU-8 master mold causes peeling of PDMS from the master mold after curing difficult. Therefore, to prevent the direct bonding of PDMS to the master mold, the prepared master mold was coated with a thin layer of silane using inductively coupled plasma.

PDMS microfluidic device was fabricated using soft lithography. The fabrication involved two steps: casting and curing of PDMS and bonding of PDMS to microscopic cover slip.

Initially, to prepare PDMS, 10:1 ratio by weigh of sylgard 184 silicone base and curing agent was mixed well. To remove the air bubbles formed in the PDMS, the mixture was degassed using desiccator connected to vacuum. The degassed mixture was then poured over the master mold which is placed in a heat-tolerant plastic tray. Subsequently, the tray with PDMS was cured in the oven for 6 hr. at 60° C. After bringing down to room temperature, the cured PDMS was gently peeled off from the master mold and then sliced it using a scalpel. Afterwards, using a biopsy puncher holes were punched to the inlet and outlets of the microfluidic with the help of stereomicroscope.

PDMS was bonded to the microscopic glass cover slip (24 mm×60 mm) using oxygen plasma bonding followed by thermal treatment. The hydrophobic nature of PDMS makes it difficult to bond PDMS to glass or any substrate. When exposed to oxygen plasma PDMS becomes hydrophilic and reactive, which helps to form an irreversible bonding between the glass and PDMS. Prior to the plasma bonding, both PDMS and cover slip were cleaned using isopropanol and dried with air. Following the cleaning, both glass and PDMS were plasma treated for 1 min. with a power of 20 W. Immediately, PDMS was placed over the glass surface and gently pressed the PDMS over the glass using tweezer. Finally, to improve the bonding strength, the bonded PDMS-glass samples were kept in the oven at 85° C. for 20 min.

FIG. 4 illustrates a general, non-limiting, example of a system 50 utilizing the present invention. The system 50 includes a computerized system 70 configured according to the invention for executing the steps of methods 100 and 200, e.g. processing and analyzing phase image data of a biological organism and determining data indicative of the morphology of the organism. The phase image data may be input into system 70 from a phase imaging system, such as Interferometric Phase Microscopy system (IPM) 60 or from a storage device where such image data has been previously stored. Optionally, the system 50 may also include the flow chamber 10 depicted in FIG. 3D. The system 50 may also include any of the devices described in FIGS. 3A-3D. Alternatively, the system 50 may be connected to the flow chamber 10 or device 300, or any other platform designed for accommodating biological samples and specifically sperm cells.

The IPM setup 60 is well known in the art and therefore need not be described in details. Usually, an IPM system 60 includes a conventional microscope 62 and an interferometry device 64 connected to the microscope. A camera 66 may be integral with or added to the IPM system. One example of an IPM system suitable to be used in the invention has been developed by the co-inventor of the present application and is described in PCT patent application number WO 2013/140396, titled "Portable interferometric device". This system includes a conventional inverted microscope and a portable interferometric module connected between the output of the microscope and a conventional digital camera.

The computerized system 70, while connected to the IPM system 60 or storage device 82, as the case may be, receives the measured image data for performing signal processing, image digital analysis and quantitative analysis on the measured data according to the invention. In addition, the computerized system 70 may control the operation of the IPM system 60 and/or the optionally connected flow chamber 10 (via an appropriate controller utility, which is not specifically shown) as will be further detailed below. Generally, the computerized system 70 includes a communication utility 72 being in data communication (e.g. via wires or wireless signal transmission) with the IPM system 60 and/or storage device 82 for receiving measured data (phase image data, dry mass data, birefringence data and data about the refractive index of the medium in which the sperm cells are immersed) relating to label-free biological organism; a data processor and analyzer 76 (e.g., a CPU) that analyzes the measured data as described above. It should be noted that system 70 is also configured for accessing memory (internal or external) to obtain the characteristic refractive index map (previously prepared and stored as described above). The system 70 may also be configured to control the measurements (e.g., according to predefined parameters) performed by the IPM system 60 and/or the flow chamber 10 or device 300. The system 70 also typically includes a memory utility (module) 74 which saves, inter alia, the received measured data and the results of analysis of the data, and may for example also store the topographic maps (OPD, dry mass, height, birefringence), and characteristic refractive index map obtained according to the method described above. The computerized system 70 may be a conventional computer including a conventional image and signal processing software, or it may be a specialized system running a specific firmware designed to execute the measurements, processing, and analysis according to the invention. The computerized system 70 may be constituted by an application program interface (API) installable on any suitable computer device and being capable of processing received image data, using the topographic maps data and the characteristic refractive index map data, which is either stored in the device or obtained by the API via accessing the remote storage device via a communication network. Thus, generally, the computerized system 70 may be associated with a separate device or may be integrated with either the IPM 60 or the flow chamber 10 or device 300.

The analyzer unit (module) 76 may be programmed to directly extract information of the measured data received from the IPM system (e.g. the digital camera), process the extracted information data and generate an output data corresponding to differential phase contrast (DIC) and dark field images of the sperm cell, based on the IPM images, completely digitally, without additional equipment. As described above, DIC is the basis of sperm organelle morphology examination (MSOME), which cannot be or it is hard to be implemented in most fertility clinics due to the cost of equipment. The generation of the DIC and/or the dark field images may be done by software which is implemented in the computerized system 70.

The computerized system 70 may optionally include or be connected to a display/monitor 80, to present relevant and useful data, including the images and the data processed by the system, to a user (e.g., a clinician) during an examination/selection procedure.

If a flow chamber 10 is connected to the computerized system 70, the computerized system 70 may control all the operations of the opening and closure of the switchable membrane gates 24 and 44 as well as the flow of the fluid/liquid inside the chamber and the substitution of the different fluids/liquids (controlling the flow circuit) for enhancing the contrast of specific organelles. If no flow chamber 10 or device 300 is used, then the sperm sample may be accommodated on a microscope slide in a conventional way. Every operation of the system 50 may be performed on-line in real time, such as during a selection procedure using the flow chamber 10 or device 300, or offline.

The invention claimed is:

1. A method for use in sperm analysis, the method comprising:
  imaging a label-free sperm cell by interferometric phase microscopy and providing measured data comprising at least interferometric phase data of the label-free sperm cell;
  processing the measured data and determining a topographic optical phase delay (OPD) map of the label-free sperm cell;
  utilizing the OPD map to determine at least one physical parameter of the label-free sperm cell;
  utilizing the at least one physical parameter for generating a quantitative sperm quality score for the label-free sperm cell; and
  utilizing the quantitative sperm quality score to either select or discard the label-free sperm cell for use in assisted reproductive technique (ART).

2. The method of claim 1, wherein the processing of the measured data further comprises generating at least one of the following: (a) a topographic dry mass map of the label-free sperm cell and (b) a topographic height map of the label-free sperm cell; and wherein the method further comprises utilizing at least one of said topographic dry mass map or topographic height map to determine at least one additional physical parameter of the label-free sperm cell and utilizing the at least one additional physical parameter in the generating of the quantitative sperm quality score for the label-free sperm cell.

3. The method of claim 2, comprising analyzing said topographical height map for determining 3D morphology of the label-free sperm cell based on physical thickness distribution and evaluating the determined 3D morphology of the label-free sperm cell by correlating between the determined 3D morphology and theoretical data indicative of a computerized 3D morphology model of the label-free sperm cell based on at least one characteristic dimension in an image of the label-free sperm cell.

4. The method of claim 2, wherein the processing of the measured data and generating of the topographic height map of the label-free sperm cell comprise utilizing a refractive index map being characteristic of sperm cells.

5. The method of claim 4, comprising obtaining said refractive index map by processing image data of at least one labeled sperm cell.

6. The method of claim 5, wherein said processing of the image data of the at least one labeled sperm cell comprises calculating the sperm refractive index map with respect to different points in the labeled sperm cell, the different points corresponding to at least one of the following cellular compartments of the labeled sperm cell: vacuoles, nucleus, acrosome, head, neck region, midpiece and tail.

7. The method of claim 5, comprising obtaining said image data by imaging the labeled sperm cell with interferometric phase microscopy (IPM), said imaging being performed with one of the following conditions:
  (i) while sequentially immersing said at least one labeled sperm cell in a first medium having a first refractive index and in a second medium having a second different refractive index, said image data comprising first and second image data indicative of first and second phase map data, respectively;
  (ii) while immersing said at least one labeled sperm cell in a medium with a known refractive index and sequentially illuminating said at least one labeled sperm cell with a first light illumination and a second light illumination, the first and second light illuminations being different by at least one of wavelength and polarization, said image data comprising first and second image data indicative of first and second phase map data, respectively; and
  (iii) while immersing said at least one labeled sperm cell in a medium with a known refractive index, said image data comprising first image data indicative of phase map data and second image data indicative of physical thickness of said different points in the labeled sperm cell.

8. The method of claim 5, comprising: receiving the image data, the image data being indicative of a plurality of labeled sperm cells, the image data comprising interferometric phase microscopy (IPM) data and birefringence image data; processing the image data and building a training data set, the processing of the image data and building the training data set respectively comprising one or more of the following: a) generating a plurality of sperm refractive index maps corresponding to the plurality of labeled sperm cells, determining a characteristic sperm refractive index map from said plurality of the sperm refractive index maps; b) generating a plurality of sperm OPD maps corresponding to the plurality of labeled sperm cells, determining a characteristic sperm OPD map from said plurality of the sperm OPD maps; c) generating a plurality of sperm height maps corresponding to the plurality of labeled sperm cells, determining a characteristic sperm height map from said plurality of the sperm height maps; d) generating a plurality of sperm dry mass maps corresponding to the plurality of labeled sperm cells, determining a characteristic sperm dry mass map from said plurality of the sperm dry mass maps; and e) generating a plurality of sperm birefringence maps corresponding to the plurality of labeled sperm cells, and determining a characteristic sperm birefringence map from said plurality of the sperm birefringence maps.

9. The method of claim 8, comprising determining said characteristic sperm refractive index map, said characteristic sperm OPD map, said characteristic sperm height map, said characteristic sperm dry mass map and said characteristic sperm birefringence map, by averaging said corresponding plurality of sperm maps.

10. The method of claim 2, wherein the measured data further comprises a birefringence image data and the processing of the measured data further comprises generating a topographic birefringence map of the label-free sperm cell, and wherein the method further comprises utilizing said topographic birefringence map to determine at least one additional physical parameter of the label-free sperm cell, and utilizing the at least one additional physical parameter in the generating of the quantitative sperm quality score for the label-free sperm cell.

11. The method of claim 10, wherein said at least one physical parameter comprises at least one of the following: head area; total volume of the head; width and length of the head; relative area or volume of the acrosome and nucleus within the head; total dry mass of the head; dry mass of the acrosome and nucleus; volume of vacuoles within the head and their relative volume; centroid and weighted centroid of each head region and the distance between them; mean OPD of each head region; variance or standard deviation of each head region; mean anterior-posterior difference; head perimeter; parameters of analysis of organ shape including: form factor, roundness, aspect ratio, compact aspect ratio, effective diameter, circular degree, circularity ratio, degree of circularity, degree of thinness, elongation, roughness, relative position of head span, longitudinal asymmetry, anterior area distribution, head non-ellipsity, ellipse structural similarity index, anterior and posterior and net distension ratio, maximum value of normalized 2D cross-correlation, solidity, extent, Euler number, number of objects in the region minus number of holes in those objects, center coordinates, eccentricity, major and minor axis length, orientation, compactness, maximum and median and mean radiuses, minimum and maximum Ferret diameter, Zernike shape features, parameters of pixel intensity (fraction of total stain in an object at a given radius, mean fractional intensity at a given radius, variation of intensity within a ring, granularity, total and median and mean intensities, standard deviation and median absolute deviation of pixel intensity, minimum and maximum of pixel density, lower and upper quartile density), texture parameters (Haralick features, angular second moment, contrast, correlation, variance, inverse difference moment, average and variance of normalized grayscale image, sum and difference of entropy); midpiece width; midpiece length; tail length; presence of cytoplasmic droplets; tail form and head form.

12. The method of claim 10, wherein said measured data comprises measured data of a plurality of label-free sperm cells, and processing of the measured data comprises building a training data set comprising at least one of the following for normal and abnormal sperm cells: said at least one physical parameter, said OPD map, data indicative of at least one of spatial, spectral and polarization state, birefringence distribution within a sperm cell, said topographic height map, said topographic dry mass map, and said topographic birefringence map.

13. The method of claim 12, comprising determining said quantitative sperm quality score, the score being indicative of a plurality of physical parameters of the label-free sperm cell, by comparing measured physical parameters of the label-free sperm cell with corresponding physical parameters of said training data set.

14. The method of claim 10, wherein said quantitative sperm quality score is indicative of at least one of chromosomal aberrations within a nucleus of the label-free sperm cell, DNA fragmentation within the label-free sperm cell and sex of the label-free sperm cell.

15. The method of claim 1, wherein said quantitative sperm quality score for the label-free sperm cell is indicative of sperm fertility.

16. A computerized system for use in sperm analysis, the system comprising:
a computer processor and a storage device, the storage device comprising software comprising a communication utility and a processor utility;
the communication utility being configured and operable for receiving measured data comprising at least interferometric phase data of a label-free sperm cell; and
the processor utility being configured and operable for: a) processing said measured data and determining a topographic optical phase delay (OPD) map of the label-free sperm cell, b) utilizing the OPD map to determine at least one physical parameter of the label-free sperm cell, c) utilizing the at least one physical parameter for generating a quantitative sperm quality score for the label-free sperm cell, and d) utilizing the quantitative sperm quality score to initiate a signal that causes the sperm cell to be selected or discarded for use in assisted reproductive technique (ART).

17. The computerized system of claim 16, wherein said quantitative sperm quality score for the label-free sperm cell is indicative of sperm fertility.

18. The computerized system of claim 16, wherein said processor utility is further configured to: a) utilize said OPD map for generating one or more of the following: a topographic dry mass map and a topographic birefringence map of the label-free sperm cell, b) utilize the topographic dry mass map and/or the topographic birefringence map to determine at least one additional physical parameter of the label-free sperm cell, and c) utilize the at least one additional physical parameter in the generating of the sperm quantitative quality score for the label-free sperm cell.

19. The computerized system of claim 16, wherein said processor utility is further configured and operable for: a) utilizing the measured data and a characteristic refractive index map of a sperm cell, stored in a memory, to calculate a physical thickness distribution of different points in said measured label-free sperm cell, b) generating a topographic height map for the label-free sperm cell, c) utilizing the topographic height map to determine at least one additional physical parameter of the label-free sperm cell, and d) utilizing the at least one additional physical parameter in the generating of the sperm quantitative quality score for the label-free sperm cell.

20. The computerized system of claim 16, comprising a memory utility configured and operable to store at least one of said measured data, results of analysis of the measured data, and a characteristic refractive index map of sperm cells.

* * * * *